United States Patent
Sakaguchi et al.

(10) Patent No.: US 7,488,474 B2
(45) Date of Patent: Feb. 10, 2009

(54) METHOD FOR DETECTING REGULATORY T CELLS USING EXPRESSION OF FOLATE RECEPTOR 4 AS INDICATOR, METHOD FOR TREATING DISEASES USING THE DETECTION METHOD, PHARMACEUTICAL COMPOSITION FOR IMMUNOSTIMULATION, AND METHOD FOR TREATING DISEASES USING THE COMPOSITION

(75) Inventors: Shimon Sakaguchi, Kyoto (JP); Keiji Hirota, Kyoto (JP); Tomoyuki Yamaguchi, Kyoto (JP)

(73) Assignees: Kyoto University, Kyoto-fu (JP); Riken, Saitama-ken (JP)

( * ) Notice: Subject to any disclaimer, the term of this patent is extended or adjusted under 35 U.S.C. 154(b) by 235 days.

(21) Appl. No.: 11/240,361

(22) Filed: Oct. 3, 2005

(65) Prior Publication Data
US 2006/0246063 A1    Nov. 2, 2006

(30) Foreign Application Priority Data
May 2, 2005    (JP)    ............................. 2005-134279

(51) Int. Cl.
*A01N 63/00*    (2006.01)
(52) U.S. Cl. .................................................. 424/93.71
(58) Field of Classification Search ........................ None
See application file for complete search history.

(56) References Cited

OTHER PUBLICATIONS

Gattinoni et al., 2006, Nat Rev Immunol. vol. 3: pp. 1-25.*
Foster et al., 2006, Expert Opin. Biol. Ther. vol. 6: 215-229.*
Jun. 2007, J Clin Invest. vol 117: 1466-1476.*
Sakaguchi et al, *J. of Immunology*, 155:1151-1164 (1995).
Shimizu et al, *J. of Immunology*, 163:5211-5218 (1999).
Nishimura et al, *International Immunology*, 16(8):1189-1201 (2004).
Yagi et al, *International Immunology*, 16(11):1643-1656 (2004).
Shimizu et al, *Nature Immunology*, 3(2):135-142 (2002).
Hori et al, *Science*, 299:1057-1061 (2003).
Hoffman et al, *Blood*, 104(3):895-903 (2004).
Spiegelstein et al, *Gene*, 258:117-125 (2000).

* cited by examiner

*Primary Examiner*—G. R. Ewoldt
*Assistant Examiner*—Amy E Juedes
(74) *Attorney, Agent, or Firm*—Sughrue Mion, PLLC

(57) ABSTRACT

An object of the present invention is to provide a technique to distinguish between $T_{reg}$ cells and activated T cells in a live state. Another object of the present invention is to provide a pharmaceutical composition for immunostimulation that can reduce the number of $T_{reg}$ cells in vivo and effectively express the immune response of activated T cells. In the method of the present invention, $T_{reg}$ cells are detected from test cells containing (i) regulatory T cells and (ii) at least one type of cell selected from the group consisting of naive T cells and activated T cells, wherein expressions of folate receptor 4 on the surfaces of cells are measured and $T_{reg}$ cells are detected using the expressions as an indicator. The present invention uses anti-folate receptor 4 antibody or folate receptor 4-binding fragment as an active ingredient contained in a pharmaceutical composition for immunostimulation.

3 Claims, 12 Drawing Sheets

Fig. 11
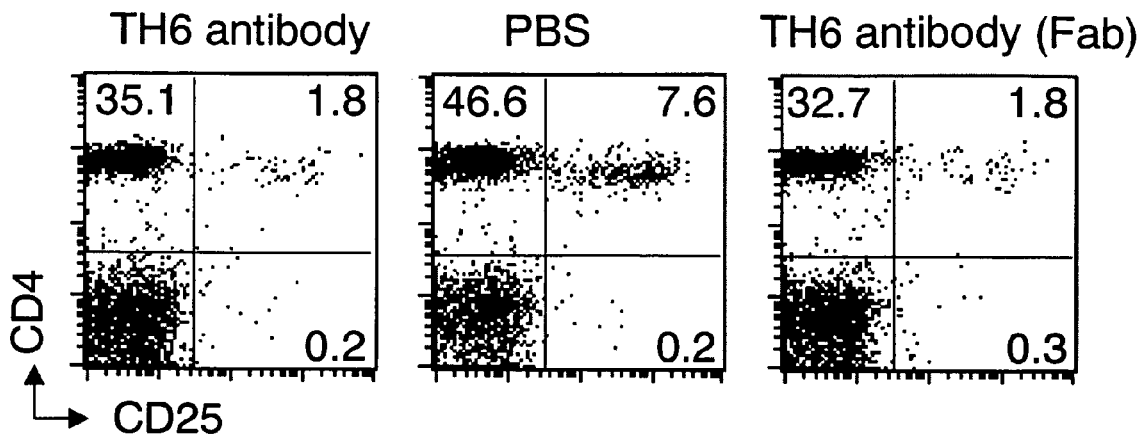
Fig. 12
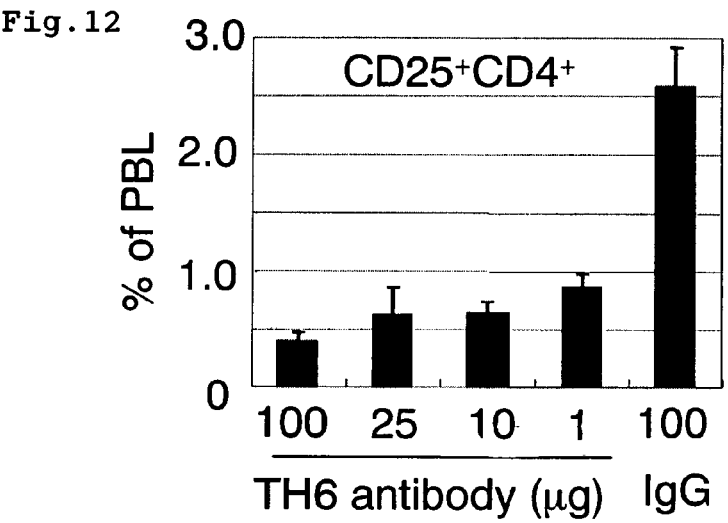
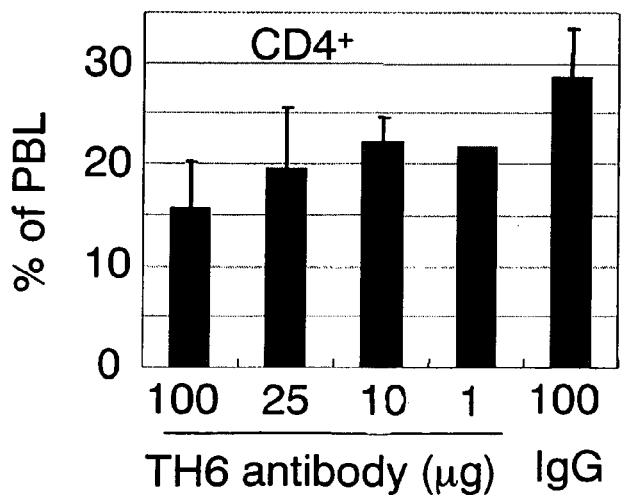

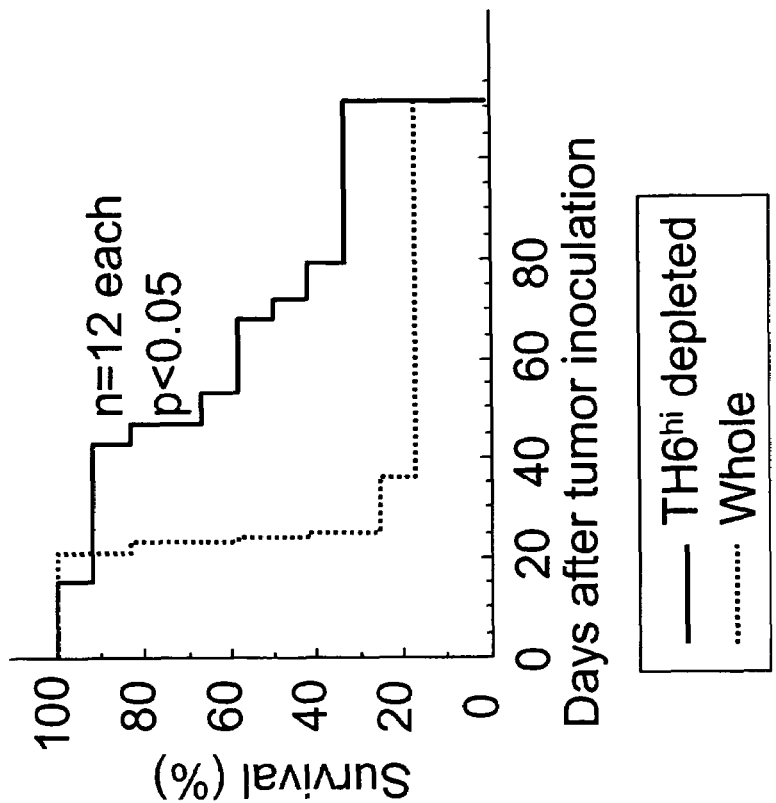
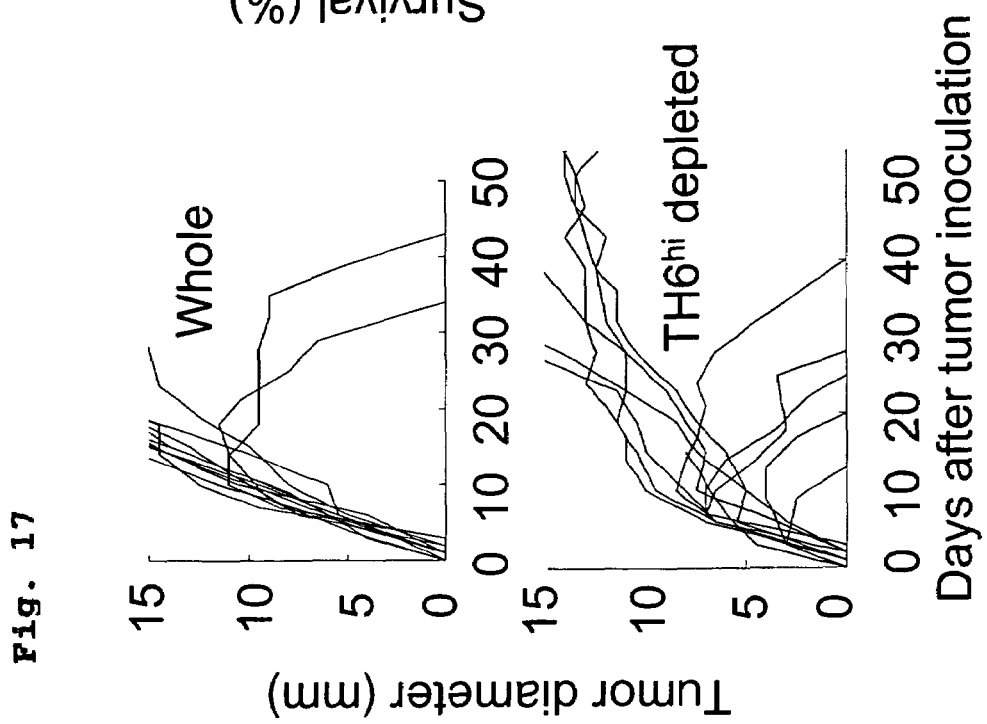
Fig. 17

METHOD FOR DETECTING REGULATORY T CELLS USING EXPRESSION OF FOLATE RECEPTOR 4 AS INDICATOR, METHOD FOR TREATING DISEASES USING THE DETECTION METHOD, PHARMACEUTICAL COMPOSITION FOR IMMUNOSTIMULATION, AND METHOD FOR TREATING DISEASES USING THE COMPOSITION

TECHNICAL FIELD

The present invention relates to a method for detecting regulatory T cells, a method for isolating regulatory T cells, a method for treating diseases using these detection and isolation methods, and a reagent for detecting regulatory T cells.

The present invention also relates to a pharmaceutical composition for immunostimulation that can effectively express the immune response of activated T cells by reducing the number of regulatory T cells, and an immunostimulation method using the composition.

BACKGROUND ART $CD4^+CD25^+$ T cells are called regulatory T cells (hereunder referred to as "$T_{reg}$ cells"), and it is known that such T cells have an immunosuppressive activity and play an important role in maintaining immunological tolerance (for example, see Sakaguchi, S., et al., 1995, "Immunologic self-tolerance maintained by activated T cells expressing IL-2 receptor alpha-chains (CD25). Breakdown of a single mechanism of self-tolerance causes various autoimmune diseases." J. Immunol. 155, 1151-1164). Because such $T_{reg}$ cells give an immune response adverse to that of activated T cells, it is reported that immunoactivation or immunosuppression can be more effectively achieved by distinguishing between $T_{reg}$ cells and activated T cells and applying them clinically (see, for example, Shimizu, J., et al., 1999, "Induction of tumor immunity by removing $CD25^+CD4^+$ T cells: a common basis between tumor immunity and autoimmunity.", J. Immunol. 163, 5211-5218). For example, it has been reported that $CD25^+$ T cells derived from normal mice having very low expressions of activated T cells are useful in maintaining immunologic tolerance after organ transplantation (Nishimura, E., Sakihama, T., Setoguchi, R., Tanaka. K., and Sakaguchi, S.: Induction of antigen-specific immunologic tolerance by in vivo and in vitro antigen-specific expansion of naturally arising CD25+CD4+ regulatory T cells. Int. Immunol. 16: 1189-1201, 2004). Similar results have been reported in humans. (Yagi, H., Nomura, T., Nakamura, K., Kitawaki, T., Hori, S., Maeda, M., Onodera, M., Uchiyama, T., Fujii, S., and Sakaguchi, S.: Crucial role of FOXP3 in the development and function of human CD25+CD4+ regulatory T cells. Int. Immunol. 16: 1643-1656, 2004). Therefore, in order to clinically apply $T_{reg}$ cells, it is necessary to establish a technique that distinguishes between $T_{reg}$ cells and activated T cells.

Several methods for distinguishing between $T_{reg}$ cells and activated T cells have been reported using substances expressed on $T_{reg}$ cells as indicators. For example, CD25 is expressed on $T_{reg}$ cells at extremely high levels, and therefore it has been reported that $T_{reg}$ cells can be collected by isolating T cells having extremely high CD25 expressions (Hoffmann P, Eder R, Kunz-Schughart L A, Andreesen R, Edinger M. Large-scale in vitro expansion of polyclonal human CD4 (+)CD25 high regulatory T cells. Blood. 104:895-903, 2004). Furthermore, CD25 and GITR have been reported to be expressed on $T_{reg}$ cells at high levels (see Shimizu, J., et al., 2002, "Stimulation of CD25(+)CD4(+) regulatory T cells through GITR breaks immunological self-tolerance", Nat. Immunol. 3, 135-142). However, because CD25 and GITR are expressed not only on $T_{reg}$ cells but also on activated T cells at high levels, it is known that CD25 and GITR cannot be used with high accuracy as indicators for distinguishing between $T_{reg}$ cells and activated T cells. There is another report stating that Foxp3 is specifically expressed in $T_{reg}$ cells (see Hori, S., et al., 2003, "Control regulatory T cell development by the transcription factor Foxp3.", Science 299, 1057-1061). However, since Foxp3 is a transcription factor, which is not expressed on the surface of cells, it is impossible to clinically use a T cell population from which $T_{reg}$ cells have been removed or isolated $T_{reg}$ cells in a live state by employing a method wherein $T_{reg}$ cells are isolated or removed using Foxp3 as an indicator. As described above, it is impossible to isolate or remove $T_{reg}$ cells by detecting and distinguishing the $T_{reg}$ cells from activated T cells in a live state using prior art techniques.

Furthermore, there is no report to date regarding not only a technique for isolating or depleting live $T_{reg}$ cells but also a technique by which the number of $T_{reg}$ cells is selectively reduced in vivo.

DISCLOSURE OF THE INVENTION

An object of the present invention is to provide a technique for distinguishing between $T_{reg}$ cells and activated T cells in a live state. Another object of the present invention is to provide a method for treating malignant tumors or infectious diseases or for suppressing immunity after organ transplantation, using above-mentioned technique.

Still another object of the present invention is to provide a pharmaceutical composition that effectively expresses the immune response of activated T cells by reducing the number of $T_{reg}$ cells in vivo, and a method for activating immunity and for treating disease using the pharmaceutical composition.

The present inventors conducted extensive research for achieving the above objects and found that $T_{reg}$ cells are expressed on the surface of folate receptor 4 (folate receptor δ, folate binding protein 3) at higher levels than activated T cells and naive T cells, and therefore $T_{reg}$ cells can be distinguished from activated T cells and naive T cells using the expression of folate receptor 4 on the surface of the cell as an indicator. Furthermore, an anti-folate receptor 4 antibody or a folate receptor 4-binding fragment, which is used for specifically detecting $T_{reg}$ cells, has an effect for reducing $T_{reg}$ cells in vivo, stimulating immunity activity in vivo, and in particular an effect for treating tumors or infectious diseases. The present invention was accomplished based on these findings and by adding improvements thereto.

In other words, with respect to a technique that detects or isolates regulatory T cells, the present invention provides the following inventions:

Item 1. A method for detecting regulatory T cells from test cells containing (i) regulatory T cells and (ii) at least one type of cell selected from the group consisting of naive T cells and activated T cells, the method comprising the steps of measuring expressions of folate receptor 4 on the surfaces of the test cells and detecting regulatory T cells using the expressions as an indicator.

Item 2. A detection method according to Item 1, wherein the expressions of folate receptor 4 are measured using anti-folate receptor 4 antibody or folate receptor 4-binding fragment.

Item 3. A method for isolating regulatory T cells comprising the step of isolating cells contained in a cell group having the most intensive folate receptor 4 expressions from test cells containing (i) regulatory T cells, and (ii) at least one type of cell selected from the group consisting of naive T cells and activated T cells.

Item 4. An isolation method according to Item 3, wherein the test cells are those comprising T cells isolated from a mammal or comprising cells obtained by subjecting naive T cells to antigenic stimulus.

Item 5. A method for treating malignant tumors or infectious disease comprising:

step (a) collecting cells containing T cells from a patient suffering from malignant tumors or infectious diseases;

step (b) obtaining cells containing T cells from which regulatory T cells have been removed by depleting cells contained in a cell group having the most intensive folate receptor 4 expressions from the cells obtained in the step (a); and step (c) administering the cells obtained in the step (b) to the patient.

Item 6. A method for suppressing immunity after organ transplant comprising:

step (a) collecting cells containing T cells from a patient received an organ transplant;

step (b) obtaining regulatory T cells by isolating cells contained in a cell group having the most intensive folate receptor 4 expressions from the cells obtained in the step (a) or cells in which regulatory T cells were induced by subjecting the cells obtained in the step (a) to antigenic stimulus; and step (c) administering regulatory T cells obtained in the step (b) to the patient.

Item 7. A method for treating autoimmune diseases comprising:

step (a) collecting cells containing T cells from a patient suffering from an autoimmune disease;

step (b) obtaining regulatory T cells by isolating cells contained in a cell group having the most intensive folate receptor 4 expressions from the cells obtained in the step (a) or cells in which regulatory T cells were induced by subjecting the cells obtained in the step (a) to antigenic stimulus; and step (c) administering regulatory T cells obtained in the step (b) to the patient.

Item 8. A reagent for detecting regulatory T cells comprising anti-folate receptor 4 antibody or folate receptor 4-binding fragment.

The present invention also provides the following inventions with respect to the technique that selectively reduces the number of regulatory T cells in vivo:

Item 9. A pharmaceutical composition for immunostimulation comprising anti-folate receptor 4 antibody or folate receptor 4-binding fragment.

Item 10. An pharmaceutical composition for treating tumors comprising anti-folate receptor 4 antibody or folate receptor 4-binding fragment.

Item 11. An immunostimulation method comprising the step of administering an amount of anti-folate receptor 4 antibody or folate receptor 4-binding fragment effective for activating immunity to a mammal including human.

Item 12. A method for treating a patient suffering from a malignant tumor or infectious disease comprising the step of administering an amount of anti-folate receptor 4 antibody or folate receptor 4-binding fragment effective for treating malignant tumor to the patient.

BRIEF DESCRIPTION OF THE DRAWINGS

In FIG. 1, the left chart shows the results obtained using TH6 antibody, and the right chart shows the results obtained using IgG2b (control). In FIG. 1, folate receptor 4 (hereunder, folate receptor 4 may be referred to as FLR4)-vector transfected cells (referred to as FLR4 in the figure) are shown by a solid line, and cells introduced to only empty vectors (referred to as Mock in the figure) are shown as shade. In both the left and right charts in FIG. 1, the vertical axis indicates PE fluorescence intensities per cell and the horizontal axis indicates the numbers of cells.

In FIG. 2, the horizontal axis indicates the numbers of cells and the vertical axis indicates APC fluorescence intensities per cell.

In FIG. 3, the horizontal axis indicates the numbers of cells and the vertical axis indicates APC fluorescence intensities per cell.

In FIG. 4, the left chart shows the results when the $CD4^+$ cells before antigenic stimulus were used as a test sample and the right chart shows the results when the $CD4^+$ cells after antigenic stimulus were used as a test sample. In both the left and right charts of FIG. 4, the horizontal axis indicates Alexa Fluor488 fluorescence intensities and the vertical axis indicates PE fluorescence intensities.

In FIG. 6, the left chart shows the expressions of CD25 and folate receptor 4 in $CD4^+$ cells derived from spleens or lymph nodes of BALB/c mice measured without antigenic stimulus and the right chart shows those after antigenic stimulus. In both the right and left charts of FIG. 6, the horizontal axis indicates PE fluorescence intensities, and the vertical axis indicates Alexa Fluor488 fluorescence intensities.

In FIG. 7, the vertical axis indicates the relative expressions of foxp3 gene with the expression of foxp3 gene in the cell group a being defined as 100.

In FIG. 8, the vertical axis indicates the amount of radioactive substance in Cpm (counts per minute)

In FIG. 9, the vertical axis indicates the amount of radioactive substance in Cpm (counts per minute).

In FIG. 10, the horizontal axis indicates the days after initiation of the experiment and the vertical axis indicates the proportion of mice in which a skin graft is favorably adhered (Graft Survival, %).

FIG. 11 shows the results of Experiment 1 in Example 3 in which expressions of CD25 and CD4 were measured in lymph-node cells collected from mice to which Fab fragments of TH6 antibody (left chart), PBS (middle figure), or TH6 antibody (right chart) were intravenously administered.

FIG. 12 shows the results of Experiment 2 in Example 3 wherein percentages of $CD25^+CD4^+$ cell fractionations (upper chart) and percentages of $CD4^+$ cell fractionations (lower chart) were measured with respect to peripheral blood collected from mice to which TH6 antibody or rat IgG were intravenously administered.

In FIG. 13, the vertical axis indicates OD405 nm values; each ○ indicates a mouse serum OD405 nm value; and the line in the figure indicates the mean value of the OD405 nm of the normal BALB/c mouse sera.

In FIG. 15, A shows the results obtained by administering fibroblastoma Meth A cells and TH6 antibody or rat IgG on the same day; B shows the results obtained by administering TH6 antibody or rat IgG to mice having tumors of at least 4 mm of axial length after inoculation with fibroblastoma Meth A cells; and C shows the results obtained by administering TH6 antibody or rat IgG to mice having tumors of at least 3 mm of axial length after administering coloncarcinoma Colon 26 cells. In FIG. 15, top and middle figures show change in average tumor diameter (the vertical axes indicate average tumor axial lengths, the horizontal axes indicate the numbers of days after administration; the top figures show the results when TH6 antibody was administered and the middle figures show the results when rat IgG was administered), and the bottom figures show the survival rate of mice after tumor inoculation.

In FIG. 16, figures show CD25 and folate receptor 4 expressions in cells, from the left to right, T cells without TH6 antibody (whole), $CD4^+$ cells, $CD8^+$ cells, and TH6 highly depleted cells ($TH6^{hi}$ depleted). In FIG. 16, the horizontal axes indicate PE fluorescence intensities and the vertical axes indicate FITC fluorescence intensities.

FIG. 17 shows the results of Experiment II of Example 5 in which a T cell group without TH6 antibody (whole) was added or a T cell group that had been treated using TH6 antibody or complement thereof ($TH6^{hi}$ depleted) was administered to mice together with fibroblastoma Meth A cells. In FIG. 17, the left charts show the changes in average tumor axial lengths and the right chart shows the survival rate after tumor inoculation.

In FIG. 18, the vertical axis indicates measured values of OD405 nm; each ○ indicates an OD405 nm value measured in mouse serum; the line in the figure indicates the mean OD405 nm value of normal BALB/c mice sera.

Figure 1:
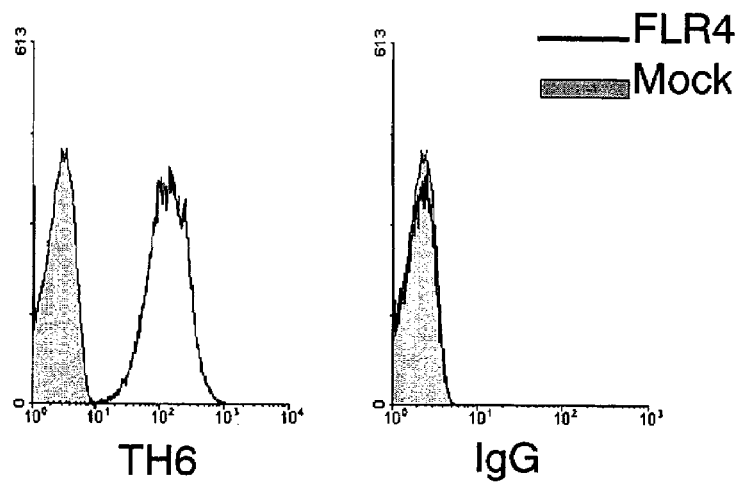
FIG. 1 shows the results of Reference Example 3, i.e., the TH6 antibody reaction specificity.

(I) DETECTION AND ISOLATION OF $T_{reg}$ CELLS

The method for detecting $T_{reg}$ cells of the present invention is such that $T_{reg}$ cells are detected from cells (hereinafter referred to as "test cells") comprising (i) $T_{reg}$ cells, and (ii) naive T cells and/or activated T cells. The detection method comprises the steps of measuring expressions of folate receptor 4 on the surfaces of T cells in the test cells, and detecting $T_{reg}$ cells using the measured expressions of folate receptor 4 as an indicator.

The method for detecting $T_{reg}$ cells of the present invention is such that $T_{reg}$ cells are specifically detected in the test cells by distinguishing (i) $T_{reg}$ cells from (ii) naive T cells and/or activated T cells. The test cells in this detection method are not limited as long as they comprise (i) $T_{reg}$ cells and (ii) naive T cells and/or activated T cells. Specific examples of test cells to be used are those comprising T cells isolated from mammals, and those comprising cells obtained by subjecting naive T cells isolated from mammals to antigenic stimulus.

In the present invention, the test cells may include hematopoietic cells, lymph-node cells, etc., in addition to T cells. Since cells other than T cells have low expressions of folate receptor 4, even if cells other than T cells are included in the test cells, such cells will not adversely affect the accuracy of $T_{reg}$ cell detection.

In the method for detecting $T_{reg}$ cells of the present invention, expression of folate receptor 4 on the surfaces of T cells can be measured by a known method. Examples of such methods are those using antigen antibody reactions; ligands binding to folate receptor 4; and techniques for in situ hybridization.

The above-mentioned method for measuring expressions of folate receptor 4 on the surfaces of T cells using an antigen antibody reaction can be specifically conducted by using anti-folate receptor 4 antibody, and subjecting the anti-folate receptor 4 antibody to antigen antibody reaction with folate receptor 4 on T cells in the test cells, and detecting the antibody bound to the folate receptor 4.

Here, the anti-folate receptor 4 antibody used may be either of monoclonal antibody or polyclonal antibody; however, monoclonal antibody is preferable. Such anti-folate receptor 4 polyclonal antibody can be obtained by immunizing a mouse, hamster, rabbit or like mammal using folate receptor 4 or $T_{reg}$ cells as immunogen, and collecting anti-folate receptor 4 polyclonal antibody from the immunized animal by a conventional method. Anti-folate receptor 4 monoclonal antibody can be obtained by culturing hybridoma cells that produce anti-folate receptor 4 monoclonal antibody. Hybridoma cells that produce anti-folate receptor 4 monoclonal antibody can be prepared by collecting cells that produce anti-folate receptor 4 monoclonal antibody from an animal immunized with folate receptor 4, folate receptor 4-expressing cells, or $T_{reg}$ cells, and fusing such cells with myeloma cells using a cell fusion method. This is an established technique in the art. Note that TH6 cell strain (FERM BP-10382) is deposited with the International Patent Organism Depositary, National Institute of Advanced Industrial Science and Technology as a mouse-rat hybridoma that can produce antibody against a folate receptor 4 of mouse origin.

It is also possible to use an anti-folate receptor 4-binding fragment such as Fab fragment and F(ab')$_2$ fragment of anti-folate receptor 4 antibody instead of anti-folate receptor 4 antibody. Such folate receptor 4-binding fragment can be prepared by known methods.

For detection purposes, the above-described antibody or fragment thereof may be directly labeled with standard marker(s) or indirectly labeled through a second antibody to which a marker is bound.

Markers used for labeling the antibody are not limited, and, for example, $^{125}$I, $^{3}$H, $^{14}$C and like radioactive isotopes; alkaline phosphatase, peroxidase and like enzymes; phycoerythrin (PE), fluorescein isothiocyanate (FITC), tetramethylrhodamine isothiocyanate (RITC) and like fluorescent materials; biotin, etc., can be used. Labeling using such markers can be conducted by known methods.

In the above-mentioned method using an antigen antibody reaction, the conditions for the antigen antibody reaction can be suitably selected from typically-employed conditions, and the method for detecting antibody binding to folate receptor 4 can also be suitably selected depending on the types of the markers labeling the antibody.

Measurements of expressions of folate receptor 4 on the surface of T cells using ligands binding to folate receptor 4 may be conducted using ligands binding to folate receptor 4 instead of antibody in the method using antigen antibody reactions. The ligands binding to folate receptor 4 are not limited and known ligands and ligands obtained by known methods may be used. The conditions employed in such methods can be suitably selected depending on the types of ligands used and the types of markers.

Measurement of expressions of folate receptor 4 on the surface of T cells using a technique of in situ hybridization can be conducted by a standard method. As a specific example, the expressions of folate receptor 4 can be measured by using a labeled probe for mRNA of folate receptor 4, hybridizing the labeled probe with mRNA of folate receptor 4 in the test cells, and detecting the labeled probe which hybridized with the mRNA. Labeled probes used in such in situ hybridization have a sequence specifically complementary to mRNA of folate receptor 4, and have a marker bound to ease detection. It is preferable that such probes have base sequences that have a low cross-reactivity with other RNAS; such probes can be prepared by cutting known folate receptor 4 cDNAs. Markers for labeling the probes are not limited and, for example, $^{125}$I, $^{3}$H, $^{14}$C, and like radioactive isotopes; FITC, RITC, and like fluorescent materials; digoxigenin; biotin, etc., can be used. Such markers can be bound to probes by methods known in the art. In in situ hybridization, conditions for pretreatment (immobilization) of the test cells, hybridization conditions, conditions for detecting markers, etc., can be suitably selected in accordance with methods known in the art.

Among the above-described methods for measuring the expressions of folate receptor 4, preferable are those using antigen antibody reactions and ligands binding to folate receptor 4. By employing such methods, it is possible to measure expressions of folate receptor 4 in the test cells in a live state. Among these methods, methods using antigen antibody reactions are the most preferable.

Using the thus-measured expressions of folate receptor 4 on T cells as an indicator enables $T_{reg}$ cells to be detected separately from naive T cells and activated T cells. In other words, based on the expressions of folate receptor 4, it is possible to detect in the test cells two or three separated cell groups comprising (1) $T_{reg}$ cells, and (2) activated T cells and/or naive T cells; or two separated cell groups comprising (1) $T_{reg}$ cells, and (2) mixture of activated T cells and naive T cells. $T_{reg}$ cells, activated T cells, and naive T cells exhibit degrees of expression of folate receptor 4 from greatest to least in this order. Among the above-mentioned cell groups to be detected, $T_{reg}$ cells are contained in the cell group that exhibits the greatest expression of folate receptor 4.

Among the test cells, $T_{reg}$ cells, activated T cells, and naive T cells tend to have CD25 expressions from greatest to least in that order, and therefore in the detection method of the present invention, differentiation of $T_{reg}$ cells, activated T cells, and naive T cells can be conducted more accurately by using expressions of CD25 in addition to those of folate receptor 4 as an indicator. In other words, by using expressions of both folate receptor 4 and CD25 as indicators, it is possible to separate the test cells into three cell groups, i.e., a cell group comprising $T_{reg}$ cells, a cell group comprising activated T cells, and a cell group comprising naive T cells. Note that CD25 expressions can be measured by known methods such as using anti-CD25 antibody, etc.

Isolation of $T_{reg}$ cells from test cells can be conducted by known methods. A preferable example of such an isolation method is that $T_{reg}$ cells are isolated from the test cells based on the expression levels of folate receptor 4 using a flow cytometer with a sorting function. Another example of an isolation method is such that $T_{reg}$ cells are isolated from the test cells using magnetic beads.

Since the method of the present invention can isolate $T_{reg}$ cells and distinguish between $T_{reg}$ cells and activated T cells, it is possible to clinically apply $T_{reg}$ cells and activated T cells with these being separated.

Malignant tumors, infectious disease, etc., can be treated by effectively expressing the action of activated T cells in the body of the patient by, for example, following steps:

collecting cells containing T cells from a patient suffering from malignant tumors, infectious disease, etc.;

subjecting the collected cells to, if necessary, antigenic stimulus to induce activated T cells; and administering the cells from which $T_{reg}$ cells has been removed using the method of the present invention to the patient.

In other words, the present invention provides a method for treating malignant tumors or for treating infectious diseases comprising steps (a) to (c) as described below:

step (a) collecting cells containing T cells from a patient suffering from a malignant tumor or infectious disease;

step (b) obtaining cells containing T cells from which regulatory T cells have been removed by removing the cells of the group having the greatest folate receptor 4 expression from the cells obtained in the step (a); and step (c) administering the cells obtained in the step (b) to the patient.

In the above-described treatment method, collection of cells containing T cells from a patient suffering from malignant tumors or infectious diseases in step (a) and administering of the cells from which $T_{reg}$ cells have been removed to the patient in step (c) may be conducted by methods and/or conditions known in the art.

It is also possible to enhance the immunosuppressive effect for healing autoimmune diseases by making $T_{reg}$ cells effectively exert their ability in the patient's body by following steps:

collecting cells containing T cells from a patient who has received an organ transplant or a patient suffering from an autoimmune disease;

inducing the $T_{reg}$ cells, if necessary, by subjecting the thus-collected cells to antigenic stimulus; and administering the $T_{reg}$ cells isolated using the method of the present invention to the patient.

In other words, the present invention provides an immunosuppressive method conducted after organ transplantation comprising the steps of:

step (a) collecting cells containing T cells from a patient who has received an organ transplant;

step (b) obtaining $T_{reg}$ cells by isolating cells of the cell group having the greatest folate receptor 4 expression from the cells obtained in the step (a) or cells in which $T_{reg}$ cells were induced by subjecting the cells obtained in the step (a) to antigenic stimulus; and step (c) administering $T_{reg}$ cells obtained in the step (b) to the patient.

Furthermore, the present invention provides a method for treating autoimmune diseases comprising the steps of:

step (a) collecting cells containing T cells from a patient suffering from an autoimmune disease;

step (b) obtaining $T_{reg}$ cells by isolating of the cell group having the greatest folate receptor 4 expression from the cells obtained in the step (a) or cells in which $T_{reg}$ cells were induced by subjecting the cells obtained in the step (a) to antigenic stimulus; and step (c) administering $T_{reg}$ cells obtained in the step (b) to the patient.

In the above-described immunosuppressive method and method for treating autoimmune diseases, the collection of cells containing T cells from patients in step (a) and administering the $T_{reg}$ cells to the patient in step (c) may be conducted by methods and/or conditions known in the art.

Furthermore, as described above, by using anti-folate receptor 4 antibody or folate receptor 4-binding fragment, it is possible to specifically detect $T_{reg}$ cells with those being distinguished from activated T cells. Therefore, the present invention also provides a reagent for detecting $T_{reg}$ cells that contains anti-folate receptor 4 antibody or folate receptor 4-binding fragment and, if necessary, carrier.

(II) PHARMACEUTICAL COMPOSITION FOR IMMUNOSTIMULATION

The above-described anti-folate receptor 4 antibodies or folate receptor 4-binding fragments used as reagents for detecting $T_{reg}$ cells can bind to $T_{reg}$ cells in vivo to selectively deplete $T_{reg}$ cells, and thereby the effects of activated T cells can be exerted effectively in vivo. Therefore, the present invention also provides a pharmaceutical composition for immunostimulation containing anti-folate receptor 4 antibody or folate receptor 4-binding fragment as an active ingredient.

When the pharmaceutical composition is applied to a human, it is preferable that the anti-folate receptor 4 antibody or folate receptor 4-binding fragment contained therein be genetically modified antibody (e.g., chimera antibody, humanized antibody) that have been artificially modified to reduce heterogenetic antigens against humans. Such modified antibody can be prepared using known methods. A chimeric antibody is an antibody comprising a variable region of an antibody derived from a mammal other than a human and a constant region of human antibody origin. A humanized antibody is an antibody comprising a complementarity determining region of an antibody derived from a mammal other than a human and a framework region and C region of human antibody origin.

The pharmaceutical composition is prepared by mixing anti-folate receptor 4 antibody or folate receptor 4-binding fragment with pharmaceutically acceptable base material(s) and/or carrier(s). There is no limitation on the form of the pharmaceutical composition, but injection is an example of a preferable form.

A dose of the pharmaceutical composition is an amount effective for activating immunity in vivo and is suitably selected depending on the age and sex of the patient, administration method, type of disease, etc. An example of the dose of the pharmaceutical composition for an adult per day is such that anti-folate receptor 4 antibody or folate receptor 4-binding fragments is contained in an amount of about 1-5000 mg, and preferably about 3-3000 mg.

Examples of administration routes of the pharmaceutical composition are subdermal, intramuscular, intraperitoneal, intra-abdominal, intrapleural, intravenous, etc.

The pharmaceutical composition for immunostimulation is effective for treating malignant tumors, infectious diseases, etc., and useful as an agent for treating malignant tumors or for treating infectious diseases. In particular, the pharmaceutical composition for immunostimulation is effective for treating malignant tumors, and useful as an agent for treating malignant tumors.

Furthermore, the present invention provides a method for activating immunity or treating malignant tumors or infectious diseases using anti-folate receptor 4 antibody or folate receptor 4-binding fragment.

In other words, the present invention provides an immunostimulation method of the following embodiment:

An immunostimulation method comprising a step of administering anti-folate receptor 4 antibody or folate receptor 4-binding fragment in an amount effective for activating immunity in a mammal, including a human.

Furthermore, the present invention provides a method for treating malignant tumors or infectious diseases of the following embodiment:

A method for treating malignant tumors or infectious diseases comprising a step of administering an effective amount of anti-folate receptor 4 antibody or folate receptor 4-binding fragment to a patient suffering from a malignant tumor or infectious disease.

EXAMPLES

The present invention is explained in detail with reference to Reference Examples, Examples, etc., although the present invention is not limited to these.

Reference Example 1

Preparation of Mouse Hybridoma Cells that Produce Anti-Folate Receptor 4 Antibody First, CD25$^+$CD4$^+$ T cell strains for serving as an immunogen were prepared by the following method. Spleen/lymph-node cells derived from normal BALB/c mice were placed in an RPMI culture medium containing culture supernatant (a 8-fold dilution) of hybridoma J11d (anti-24CD antibody-producing cell, purchased from the American Type Culture Collection) and culture supernatant (a 10-fold dilution) of hybridoma 3.155 (anit-CD8 antibody-producing cell, purchased from the American Type Culture Collection), and allowed to stand on ice for 30 minutes. The spleen/lymph-node cells in the RPMI culture medium were put into 10 cm dishes (2 dishes per mouse) coated with anti-rat IgG caprine antibody (product of ICN Pharmaceuticals, 5 ml/dish of anti-rat IgG caprine antibody diluted to 5 μg/ml), and incubated at 4° C. for 30 minutes. The suspension cells were then collected as cells rich in CD4$^+$ cells by a panning method. The collected cells were reacted on ice with biotin-labeled anti-CD25 antibody (clone name: 7D4, product of PharMingen Company, a 200-fold dilution), PE-labeled streptavidin (product of PharMingen Company, a 400-fold dilution), and beads-labeled anti-PE antibody (product of Miltenyi Biotec GmbH, a 10-fold dilution) in that order for 30 minutes each, and CD25$^+$ CD4$^+$ cells were then collected as a positive fraction by passing through a magnetic beads column twice. The thus-obtained cells were stimulated by being subjected to repeated co-culture with anit-CD3 antibody (10 vol % of culture supernatant of hybridoma 2C11, hybridoma 2C11 was purchased from the American Type Culture Collection), interleukin 2 (IL-2, provided by Shionogi & Co. Ltd., 200 U/ml), and splenic cells irradiated with 15 Gy radiation, obtaining CD25$^+$CD4$^+$ T cell strains.

Rats (Wister rat; product of Clea Japan, Inc.) were immunized against the thus-obtained CD25$^+$CD4$^+$ T cell strains (5×10$^6$) by intraperitoneally injecting the CD25$^+$CD4$^+$ T cell strains to the mice every two weeks (total 3 times). The spleen cells of each rat were collected three days after the final injection and subjected to cell fusion using P3U1 mouse-myeloma cells (provided by Juntendo University) and Polyethyleneglycol 4000 (product of Merck & Co., Inc., 1 g/ml). Screening of hybridomas was conducted using FACS by determining whether or not the culture supernatant can stain CD25$^+$CD4$^+$ cells more intensely than CD25$^-$CD4$^+$ cells. Specifically, CD4$^+$ lymphocytes collected from a BALB/c mouse by a panning method were reacted with each culture supernatant, reacted with FITC-labeled anti-rat IgG mouse antibody F(ab')$^2$ fragments (product of Jackson ImmunoResearch, a 1000-fold dilution), blocked with rat serum (a 50-fold dilution), reacted with PE-labeled anti-CD25 antibody (clone name: PC61, product of PharMingen Company), and then analyzed using a FACS Calibur.

Mouse hybridoma TH6 cell strain (FERM BP-10382) was thus obtained.

Reference Example 2

Preparation of Anti-Folate Receptor 4 Antibody (TH6 antibody)

The mouse hybridoma TH6 cells (5×10$^6$) obtained in Reference Example 1 were administered to the abdominal cavities of SCID mice (product of Clea Japan, Inc.), which are immunodeficient mice, and abdominal dropsy was extracted on day 10 and after from the injection. The extracted abdominal dropsy was subjected to centrifugation, cell components and the like were removed therefrom by being passed through a 0.45 μm filter (product of Millipore), and then the monoclonal antibody (TH6 antibody) was purified using Protein G column (product of Amersham Biosciences KK). Elution of monoclonal antibody from the column was conducted using 0.1 M glycine-HCl at pH 2.7. Thus-obtained solution of monoclonal antibody was subjected to dialysis with PBS using a dialysis membrane (Spectrum Laboratories, MWCO 12-14000) and filtration using 0.2 μm filter (product of Millipore), obtaining purified antibody.

Reference Example 3

Reaction Specificity of Anti-Folate Receptor 4 Antibody (TH6 Antibody)

A pMXS-IG vector (provided by the Institute of Medical Science, the University of Tokyo) obtained by incorporating full-length cDNAs of mouse folate receptor 4 (FLR4) into Plat-E cells that are subclone of human HEK293T cells (provided by the Institute of Medical Science, the University of Tokyo) or an empty pMXS-IG vector was subjected to transfection using Fugene 6 (Roche Molecular Biochemicals). Biotin-labeled TH6 antibody (labeled using an Amersham biotinization kit) or biotin-labeled IgG2b (product of PharMingen Company) was added to the cells (1×10$^8$ cells/ml) in such a manner that the content of the biotin-labeled TH6 antibody or biotin-labeled IgG2b became 1 μg/ml, and reacted on ice for 30 minutes. After washing, PE-labeled streptavidin (product of PharMingen Company) was added thereto in such a manner that the amount of the PE-labeled streptavidin became 0.5 μg/ml, reacted on ice for 30 minutes, and FACS analysis was then conducted.

FIG. 1 shows the results. In FIG. 1, the left chart shows the results when TH6 antibody was used, and the right chart shows the results when IgG2b (control) was used. In FIG. 1, FLR4-vector transfected cells (indicated as FLR4 in the figure) are shown by a solid line, and cells introduced into only empty vectors (indicated as Mock in the figure) are shown as shade. As shown in FIG. 1, the TH6 antibody obtained in Reference Example 2 bind specifically to FLR4-vector transfected cells, and therefore it was confirmed from these results that TH6 antibody specifically bind to FLR4.

Reference Example 4

Verification of Expression of Folate Receptor 4 in Thymocytes and Lymph-Node Cells <Verification of Expression of Folate Receptor 4 in Thymocytes>

Biotin-labeled TH6 antibody (labeled using an Amersham biotinization kit) or biotin-labeled IgG2b (product of PharMingen Company) were added to thymocytes (1×10$^9$ cells/ml) collected from BALB/c mice in such a manner that the content of the biotin-labeled TH6 antibody or biotin-labeled IgG2b became 1 μg/ml, and reacted on ice for 30 minutes. Subsequently, FITC-labeled anti-CD4 antibody (product of PharMingen Company), PE-labeled anti-CD8 antibodies (product of PharMingen Company) and APC-labeled Streptavidin (product of PharMingen Company) were added thereto in such a manner that the content of each became 0.4 μg/ml, reacted on ice for 30 minutes, and FACS analysis was then conducted.

Figure 2:
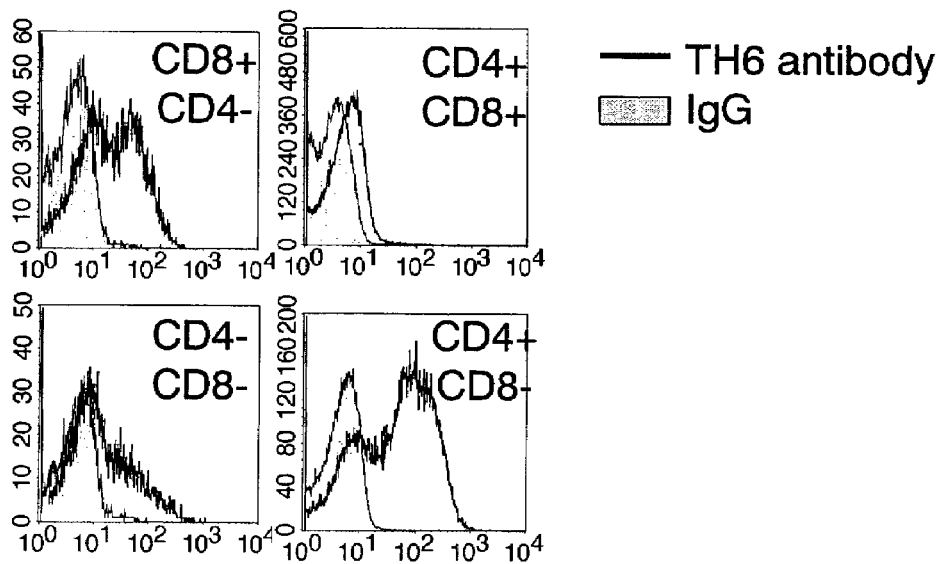
FIG. 2 shows the results of Reference Example 4 in which expressions of folate receptor 4 in thymocytes were measured. Specifically, in FIG. 2, APC fluorescence intensities in the cells of $CD8^+CD4^-$ (upper left chart), $CD8^+CD4^+$ (upper right chart), $CD8^-CD4^-$ (lower left chart), and $CD8^-CD4^+$ (lower right chart) using TH6 antibody are shown by solid lines and those using IgG2b (control) are shown as shade.

FIG. 2 shows the results. In FIG. 2, APC fluorescence intensities in the cells of CD8$^+$CD4$^-$ (upper left), CD8$^+$CD4$^+$ (upper right), CD8$^-$CD4$^-$ (lower left), and CD8$^-$CD4$^+$ (lower right) using TH6 antibody are shown by solid lines and those using IgG2b (control) are shown as shade. From the results, it became clear that in thymocytes, cells having folate receptor 4 expressions exist in CD8$^-$CD4$^+$ cell fractionations at high levels.

<Verification of Expression of Folate Receptor 4 in Lymph-Node Cells>

Biotin-labeled TH6 antibody (labeled using an Amersham biotinization kit) or biotin-labeled IgG2b (product of PharMingen Company) were added to lymph-node cells (1×10$^8$ cells/ml) collected from BALB/c mice in such a manner that the content of the biotin-labeled TH6 antibody or biotin-labeled IgG2b became 1 μg/ml, and reacted on ice for 30 minutes. Subsequently, FITC-labeled anti-CD4 antibody (product of PharMingen Company), FITC-labeled anti-CD8 antibody (product of PharMingen Company) or FITC-labeled anti-B220 antibody (product of PharMingen Company) were added thereto in such a manner that the content thereof became 0.4 μg/ml, APC-labeled Streptavidin (product of PharMingen Company) was also added thereto in such a manner that its content thereof became 0.4 μg/ml, then reacted on ice for 30 minutes, and FACS analysis was then conducted.

Figure 3:
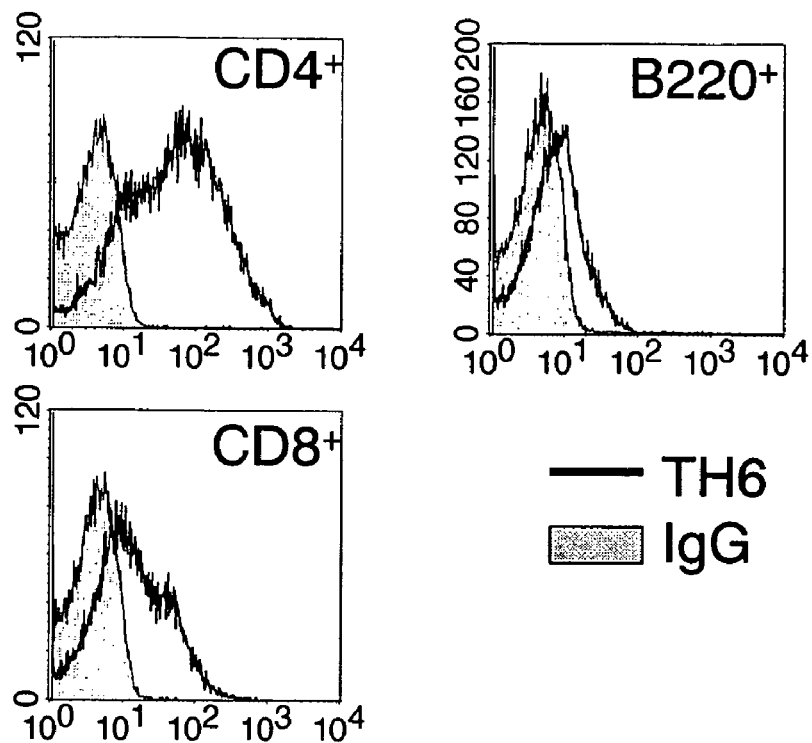
FIG. 3 shows the results of Reference Example 4 in which expressions of folate receptor 4 in lymph-node cells were measured. Specifically, in FIG. 3, APC fluorescence intensities in the cells of $CD4^+$ (upper left chart), $CD8^+$ (lower left chart), and $B220^+$ (upper right chart) using TH6 antibody are shown by solid lines and those using IgG2b (control) are shown as shade.

FIG. 3 shows the results. In FIG. 3, APC fluorescence intensities in the cells of $CD4^+$ (upper left), $CD8^+$ (lower left), and $B220^+$ (upper right) using TH6 antibody are shown by solid lines and those using IgG2b (control) are shown as shade. From the results, it became clear that, in lymph-node cells, folate receptor 4 is expressed in $CD4^+$ cells at higher levels than in $CD8^+$ cells and B cells.

Example 1-1

Detection of $T_{reg}$ Cells $CD4^+$ cells were collected from lymph-nodes and spleens of BALB/c mice by a panning method. The thus-obtained $CD4^+$ cells ($1 \times 10^6$ to $2.5 \times 10^6$ cells/ml) were stimulated by the addition of an equivalent amount of C57Bl/6 mouse-derived spleen cells irradiated with 15 Gy radiation as antigen presenting cells (APC), and also IL-2 (final concentration of 50 U/ml), and then cultured at 37° C. for 9 days.

Using $CD4^+$ cells before and after stimulation as test samples, detection of $T_{reg}$ cells was conducted by the following method.

Alexa Fluor488-labeled TH6 antibody (product of Molecular Probes, labeled using an Alexa Fluor 488 Monoclonal antibody labeling kit), PE-labeled anti-CD25 antibody (product of PharMingen Company), and CyCrome-labeled anti-CD4 antibody (product of PharMingen Company) were added to a $CD4^+$ cell-containing solution ($2 \times 10^8$ cells/ml) in such a manner that their contents became 1 μg/ml, 2 μg/ml and 0.4 μg/ml respectively, and, after being reacted on ice for 30 minutes, FACS analysis was then conducted.

Figure 4:
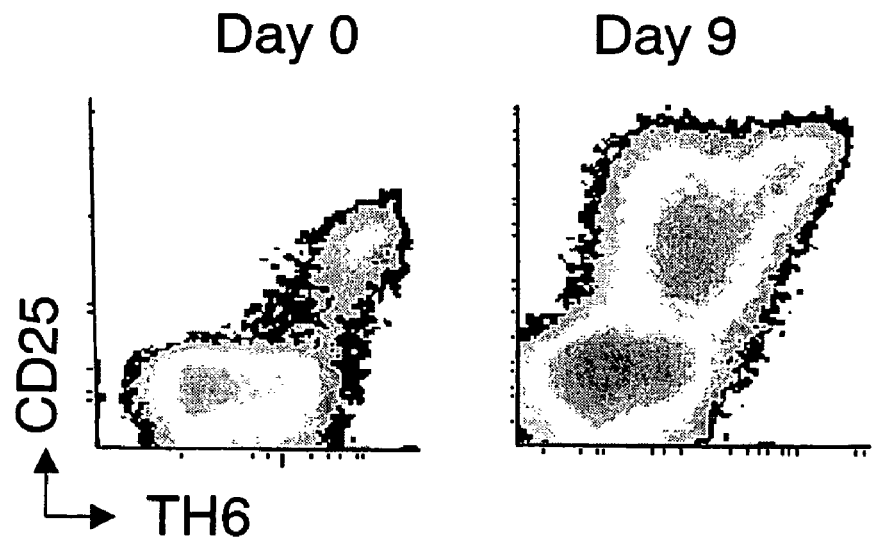
FIG. 4 shows the result of Example 1-1 in which expressions of CD25 and folate receptor 4 in $CD4^+$ cells derived from lymph nodes or spleens of BALB/c mice by a panning method before and after antigenic stimulus were measured.

FIG. 4 shows the results. In FIG. 4, the left chart shows the results when the $CD4^+$ cells before antigenic stimulus were used as a test sample and the right chart shows the results when the $CD4^+$ cells after antigenic stimulus were used as a test sample. In both the left and right charts of FIG. 4, the horizontal axis indicates Alexa Fluor488 fluorescence intensities and the vertical axis indicates PE fluorescence intensities. As is clear from FIG. 4, $CD25^+CD4^+$ cells, which are $T_{reg}$ cells, expressed folate receptor 4 at higher levels than $CD25^-CD4^+$ cells.

From these results, it was confirmed that the $CD4^+$ cells before antigenic stimulus can be divided into two fractions, one being a cell group having high expressions of folate receptor 4 and CD25, and the other being a cell group having low to medium folate receptor 4 expression and low CD25 expression. The $CD4^+$ cells after antigenic stimulus can be divided into three fractions, i.e., a cell group having high expressions of folate receptor 4 and CD25, a cell group having medium folate receptor 4 expression and medium to high CD25 expression, and a cell group having low expressions of folate receptor 4 and CD25.

Example 1-2

Detection of $T_{reg}$ Cells

Using $CD25^+CD4^+$ cells collected from a Thy1.2+ BALB/c mouse by MACS using magnetic beads and $CD25^- CD4^+$ cells collected from a Thy1.1+ BALB/c mouse by MACS using magnetic beads, the following Experiment was conducted. Using a mixture of $CD25^+CD4^+$ cells and $CD25^- CD4^+$ cells as test cells, antigenic stimulus was conducted by the same method as described in Example 1-1. Biotin-labeled ani-Thy1.2 antibody (product of PharMingen Company) were added to a sample of the cells mixture ($5 \times 10^7$ cells/ml) before stimulation (FIG. 5, the left chart) and 9 days after stimulation (FIG. 5, the right chart) in such a manner that the content of the biotin-labeled ani-Thy1.2 antibody became 0.2 μg/ml, and then reacted on ice for 30 minutes. Subsequently, Alexa Fluor488-labeled TH6 antibody (product of Molecular Probes, labeled using an Alexa Fluor 488 Monoclonal antibody labeling kit), PE-labeled anti-CD25 antibody (product of PharMingen Company) APC-labeled anti-CD4 antibody (product of PharMingen Company) and PerCpCy5.5-labeled streptavidin (product of PharMingen Company) were added thereto in such a manner that their contents became 1 μg/ml, 2 μg/ml, 0.25 μg/ml and 0.4 μg/ml respectively, reacted on ice for 30 minutes, and FACS analysis was then conducted.

Figure 5:
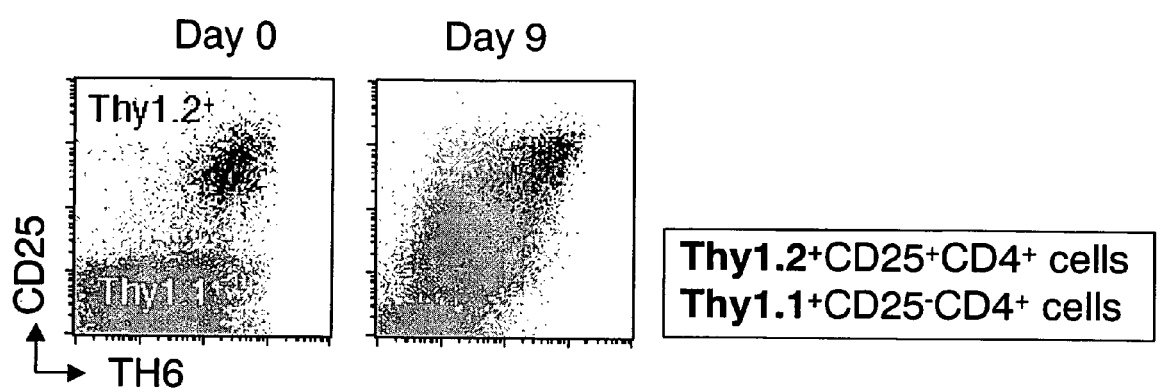
FIG. 5 shows the results of Example 1-2 in which expressions of CD25 and folate receptor 4 per cell of cells mixture of $CD25^+CD4^+$ cells and $CD25^-CD4^+$ cells before and after antigenic stimulus were measured. The left chart of FIG. 5 shows the results when the cells mixture before stimulation was used as a test sample, and the right chart shows the results when the cell mixture population after stimulation was used as a test sample. In both the right and left charts of FIG. 5, $Thy1.2^+$ cells are shown as black dots, $Thy1.2^-$ cells ($Thy1.1^+$ cells) are shown as gray dots, the horizontal axis indicates PE fluorescence intensities, and the vertical axis indicates Alexa Fluor488 fluorescence intensities.

FIG. 5 shows the results. In FIG. 5, the left chart shows the results when the cells mixture of $CD25^+CD4^+$ cells and $CD25^-CD4^+$ cells before stimulation was used as a test sample, and the right chart shows the results when the cells mixture of $CD25^+CD4^+$ cells and $CD25^-CD4^+$ cells after stimulation was used as a test sample. In both the left and right charts of FIG. 5, Thy1.2+ cells are expressed as black dots, Thy1.2 negative (Thy1.1+) cells are expressed as gray dots, the horizontal axis indicates PE fluorescence intensities, and the vertical axis indicates Alexa Fluor488 fluorescence intensities. From these results, it became clear that the $CD25^+$-derived cells could exhibit high expressions of folate receptor 4 and CD25 after being stimulated.

Example 2

Isolation of $T_{reg}$ Cells

<Cell Isolation Based on the Folate Receptor 4 Expression>

$CD4^+$ cells were collected from spleens and lymph nodes of BALB/c mice by a panning method. To the $CD4^+$ cells ($2 \times 10^8$ cells/ml), Alexa Fluor488-labeled TH6 antibody (product of Molecular Probes, labeled using an Alexa Fluor 488 Monoclonal antibody labeling kit), PE-labeled anti-CD25 antibody (product of PharMingen Company), and CyChrome-labeled anti-CD4 antibody (product of PharMingen Company) were added in such a manner that the their contents became 1 μg/ml, 2 μg/ml and 0.4 μg/ml respectively, reacted on ice for 30 minutes, and FACS analysis was then conducted (see the left chart of FIG. 6).

To $CD4^+$ cells ($2 \times 10^6$ cells/ml) collected from spleens and lymph nodes of BALB/c mice by a panning method, were added APC (spleen cells irradiated with 15 Gy X-rays) of C57Bl/6 mice in such a manner that the APC content became $2 \times 10^6$ cells/ml. IL-2 was subsequently added thereto in such a manner that the content of the IL-2 became 50 U/ml, and then cultured at 37° C. for 9 days. Cells obtained by depleting dead cells from the above-obtained cells by a density centrifugation method using Lympholyte-M (product of Cedarlane) was reacted with anti-Fc receptor antibody (culture supernatant of hybridoma2.4G2 cells; the hybridoma cells were purchased from the American Type Culture Collection) on ice for 30 minutes, and the expressions of folate receptor 4 and CD25 were analyzed using FACS (see right chart in FIG. 6) in the same manner as described above.

Figure 6:
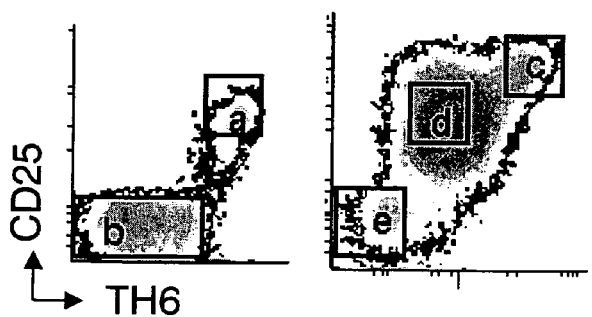
FIG. 6 shows the results of Example 2 in which expressions of CD25 and folate receptor 4 in $CD4^+$ cells derived from spleens or lymph nodes of BALB/c mice were measured.

$CD4^+$ cells whose folate receptor 4 and CD25 expressions had been measured in the above-described manner were classified into a to e cell groups as shown in FIG. 6, and each cell group was isolated using a Moflow (Dako Cytomation) to purity of 95% or greater.

<Measurement of foxp3 Gene Expressions in a to e Cell Groups>

Expressions of Foxp3 gene in cells contained in the above-obtained a to e cell groups were determined by real-time PCR assay, and the ratio of HPRT gene, which was used as an internal standard, relative to mRNA was calculated.

Quantitative determination was conducted by extracting RNAs using Isogen (product of Nippon Gene Co., Ltd.) from about $5\times10^5$ isolated cells, and subjecting the RNAs to reverse transcription using Superscript II reverse-transcriptase and oligo$(dT)_{12-18}$ primer (Invitrogen), obtaining cDNAs. Real-time PCR assay was conducted using an ABI/PRISM770 sequence detection system (PE Applied Biosystems). Primers and probes were as follows: Foxp3 primers: 5'-CCC AGG AAA GAC AGC AAC CTT-3' and 5'-TTC TCA CAA CCA GGC CAC TTG-3'; Foxp3 probe: 5'-FAM-ATC CTA CCC ACT GCT GGC AAA TGG AGT C-3'; HPRT primers: 5'-TGA AGA GCT ACT GTA ATG ATC AGT CAA C-3' and 5'-AGC AAG CTT GCA ACC TTA ACC A-3'; HPRT probe: 5'-VIC-TGC TTT CCC TGG TTA AGC AGT ACA GCC C-3', and were designed at intron/exon boundaries. Using a QuantiTect Probe PCR kit (product of Qiagen), each triplicate sample was subjected to 40 cycles each comprising 10 minutes at 95° C., 15 seconds at 95° C. and 60 seconds at 60° C. with the concentrations of primer and TaqMan probe being 0.4 µM and 0.2 µM respectively. Average amounts of mRNAs in Foxp3 and HPRT of the triplicate samples were calculated and determined as relative amounts thereof. The amount of mRNA in Foxp3 was divided by the amount of mRNA in HPRT mRNA (ratio of Foxp3/HPRT), and relative Foxp3/HPRT ratios for each fraction were determined with the Foxp3/HPRT ratio in cell group a being set as 100.

Figure 7:
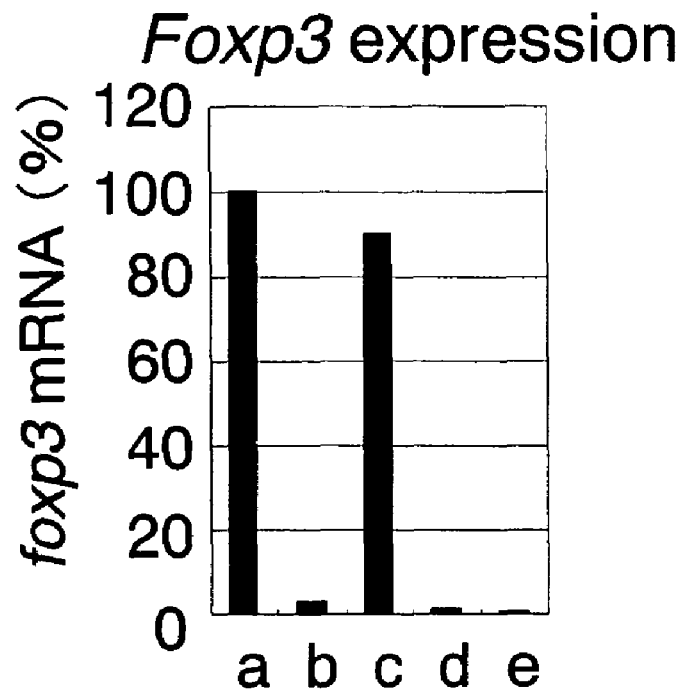
FIG. 7 shows the results of Example 2 in which expressions of foxp3 gene in the cell groups a to e of FIG. 6 were measured.

FIG. 7 shows the results. As is clear from the results, the expression of foxp3, which is a specific marker for $T_{reg}$ cells, in cell group c is essentially as high as in cell group a. It is therefore clear that the cell group c mainly contains $T_{reg}$ cells. This result also confirmed that $T_{reg}$ cells can be specifically detected and isolated using folate receptor 4 expression as an indicator.

<Restimulus to Cell Groups a to e using Alloantigen>

Cells ($1\times10^4$) from each of the thus-obtained cell groups a to e were cultured in U-bottomed 96-well plates with APC ($1\times10^5$ spleen cells irradiated with 15 Gy X-rays) derived from c57/Bl/6 mice for 5 and 7 days at 37° C. Incorporation of $^3H$ thymidine (1 µM Ci/well) during the last 6 hours of culturing was measured. The mean values of duplicates are shown with standard deviations.

Figure 8:
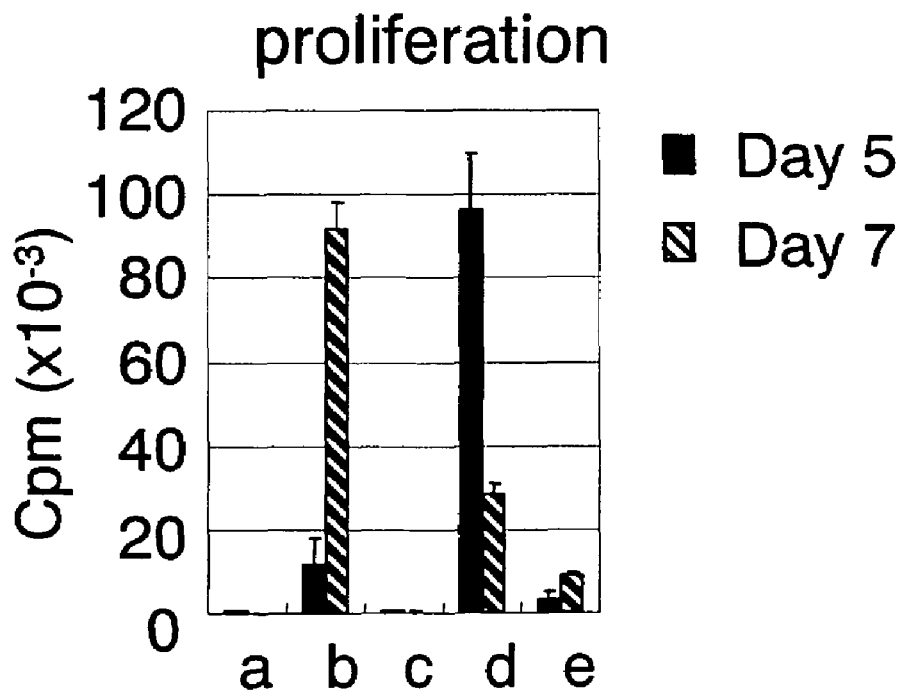
FIG. 8 shows the results of Example 2 in which incorporations of $^3$H thymidine (1 μM Ci/well) into the cell groups a to e of FIG. 6 for 6 hours until completion of cell culturing were measured after restimulating with alloantigen.

FIG. 8 shows the results. As is clear from the results, cells with high folate receptor 4 expression (cell groups a and c) did not react to the restimulus by alloantigen, but cells with medium folate receptor 4 expression and medium CD25 expression (cell group d) after restimulus exhibited high proliferation reaction against the restimulus from the early stage of reaction. Furthermore, cells with low CD25 expression (cell groups b and e) tended to exhibit a low proliferation reaction at the early stage of reaction but a relatively high proliferation reaction at the later stage of the reaction. From these results, it was confirmed that cell groups a and c mainly contain $T_{reg}$ cells, cell group d mainly contains activated T cells, and cell groups b and e mainly contain naive T cells.

<Measurement of Immunoreaction Suppression Activity>

Cell group a or c was added to cell group b ($5\times10^4$ cells/ml) in such a manner that the content of cell group a or c became $1\times10^4$ cells/ml (in FIG. 9, indicated as ⅕) or $2.5\times10^3$ cells/ml (in FIG. 9, indicated as 1/20), and cultured in C57Bl/6 mouse-derived APC ($1\times10^5$ cells/ml) for 7 days at 37° C. Incorporation of $^3H$ thymidine (1 µM Ci/well) during the last 6 hours of culturing was measured. The mean values of duplicates are shown together with standard deviations. For comparison, incorporations of $^3H$ thymidine in cells without addition of cell group a or c (in FIG. 9, shown as b, second from the right), and those without addition of any of cell groups a to c (in FIG. 9, shown as—at the right) were also measured.

Figure 9:
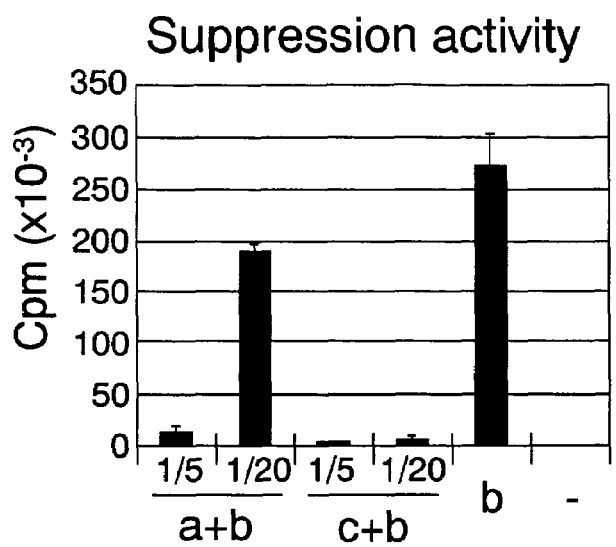
FIG. 9 shows the results of Example 2 in which immunoreaction suppression activities of the cell groups a and c of FIG. 6 were measured.

FIG. 9 shows the results. From these results, it is clear that cell group c had more intense immunoreaction suppression activity than cell group a (i.e., normal mouse $T_{reg}$ cells).

<Measurement of the Effect for Prolonging the Skin Graft>

Figure 10:
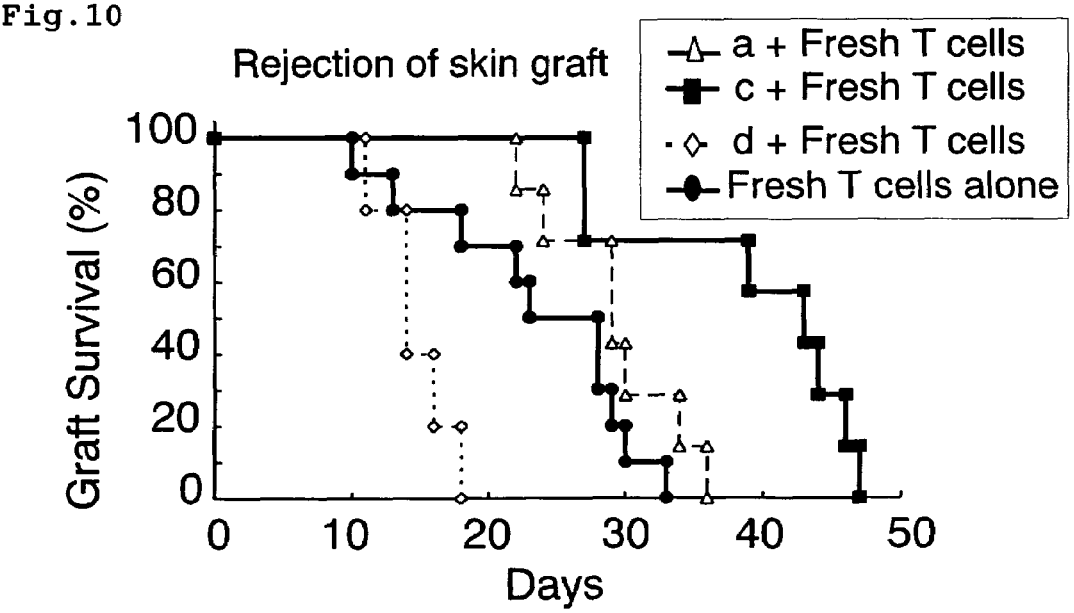
FIG. 10 shows the results of Example 2 in which the effects of the cell groups a, c and d of FIG. 6 for prolonging graft survival of allo skin grafts were measured.

Skins of C57Bl/6 mice were transplanted to BALB/c nude mice lacking T cells, and, two weeks or more after healing of the wound, $1\times10^5$ cells of cell group a, c or d together with $2\times10^5$ BALB/c T cells (cell population obtained by depleting J11d positive cells from spleen/lymph-node cells by a panning method; unstimulated cells (Fresh T cells)) were administered through intravenous injection. FIG. 10 shows the number of days until the skin grafts were rejected, counting the transplantation day as zero. For comparison, the same experiment was conducted except that the above-descried BALB/c T cells (unstimulated T cells; Fresh T cells) alone were administered through intravenous injection.

FIG. 10 shows the results. Based on these results, it was confirmed that use of cell groups a and c leads to prolongation of allo skin graft survival.

Example 3

Affect of Anti-Folate Receptor 4 Antibody (TH6 Antibody) on $T_{reg}$ Cells

<Experiment 1>

Monoclonal antibody (TH6 antibody) prepared in Reference Example 2 or Fab fragments thereof (30 µg) were diluted with 300 µl of PBS (pH7.2) and intravenously administered to BALB/c mice. Four days after administration, lymph-node cells were extracted from the mice. After blocking the obtained lymph-node cells with anti-Fc receptor antibody, the lymph-node cells were reacted with FITC-labeled anti-CD4 antibody and PE-labeled anti-CD25 antibody, and FACS analysis was then conducted. For comparison, the same experiment was conducted except that only PBS was administered to the BALB/c mice. Note that the Fab fragments of TH6 antibody used in this experiment were obtained by using an ImmunoPure Fab Preparation Kit (product of Pierce) and dialyzing the prepared Fab fragments with PBS.

FIG. 11 shows the results. From these results, it is clear that $CD25^+CD4^+$ cells (i.e., $T_{reg}$ cells) can be depleted by administering folate receptor 4 antibody or Fab fragment thereof.

<Experiment 2>

Monoclonal antibody (TH6 antibody) prepared in Reference Example 2 or rat IgG (product of Sigma Chemical Company) in an amount of 1 to 100 μg was intravenously administered to BALB/c mice. Peripheral blood was collected from the mice four days after administration, the red blood corpuscles of which were subjected to hemolyzation, CD25 and CD4 were stained in the same manner as in Experiment 1, and FACS analysis was then conducted.

FIG. 12 shows the results. FIG. 12 shows, together with the standard deviations, the mean values of proportions of $CD25^+$ $CD4^+$ cell fractions (upper chart) and of $CD4^+$ cell fractionations (lower chart) in lymphocytes fractions, which can be sorted by forward scatter light (FSC) and side scatter light (SSC). As shown in FIG. 12, by the administration of TH6 antibody, the number of $CD25^+CD4^+$ cells was dose-dependently reduced to one fifth. The number of $CD4^+$ cells was also dose-dependently reduced almost by half, but the reduction was slighter than for $CD25^+CD4^+$ cells. Based on the results of this Experiment, it was confirmed that TH6 antibody can selectively deplete $CD25^+CD4^+$ cells in vivo.

<Experiment 3>

To BALB/c mice, 100 μg of monoclonal antibody (TH6 antibody) prepared in Reference Example 2 or rat IgG (product of Sigma Chemical Company) was intra-abdominally administered on the $10^{th}$ day and $20^{th}$ day from birth. Three months after the final administration, blood sera and the stomachs were extracted from the mice. Titer of anti-gastric parietal cell autoantibody of the sera collected from the mice were measured by ELISA as follows. First, wells of a ELISA plate with 96 flat wells (product of ICN, Limbro/Titertek plate) were coated with gastric mucosa extract of BALB/c mice diluted with PBS over a night, washed with 0.05% Tween-20/PBS, blocked with 1% BSA/PBS at room temperature for 1 hour. And then, the sera collected from the mice were added into the wells that had been subjected to the above-treatment and allowed to incubate at room temperature for 1 hour. Subsequently, thus treated wells were washed with 0.05% Tween-20/PBS, and subjected reaction with ALP-labeled anti-mouse IgG (product of Sigma Chemical Company, 1/1000 dilution) at room temperature for 1 hour. Thereafter, the wells were washed with 0.05% Tween-20/PBS, ALP substrate (product of Sigma Chemical Company, 1 mg/ml) dissolved with 10 wt. % diethanol amine solution (pH 9.8) was added in to the wells and allowed to react for 30 minutes, and OD405 nm values were then measured.

Figure 13:
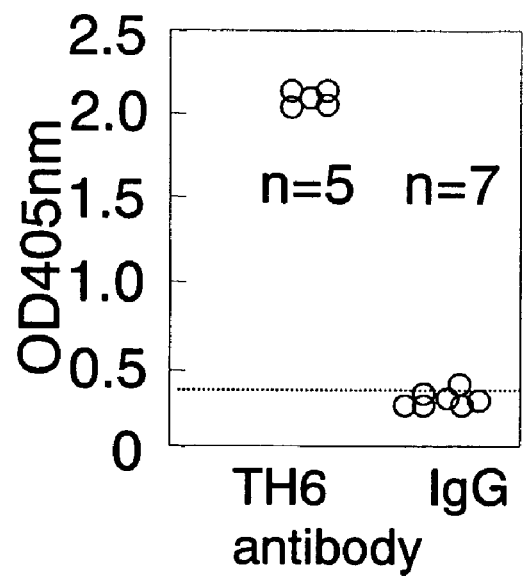
FIG. 13 shows the results of Experiment 3 in Example 3 in which anti-gastric parietal cell autoantibody titers were measured in the sera of BALB/c mice that had been administered TH6 antibody or rat IgG.

FIG. 13 shows the results. In FIG. 13, each ○ indicates a measured OD405 nm value for each mouse serum; and the line in the figure indicates the mean OD405 nm value of normal BALB/c mouse sera. From these results, it is clear that in all the mice administered with TH6 antibody, anti-gastric parietal cell autoantibody were produced at high levels.

Figure 14:
FIG. 14 shows micrographs taken while observing using a microscope of HE stained stomachs extracted from BALB/c mice that had been administered TH6 antibody or rat IgG in Experiment 3 of Example 3. The upper micrograph shows the stomach of a mouse that had been administered TH6 antibody, and the lower micrograph shows a stomach of a mouse that had been administered rat IgG.

The stomachs extracted from the mice were fixed using 10% formalin, subjected to thin sectioning, stained with HE (hematoxylin and eosin), and observed using a microscope (FIG. 14). In the mouse administered with TH6 antibody, thickening of stomach walls and elimination of gastric parietal cells (cells in the fundus which dyed deep red), and infiltration of lymphocytes were observed. In the mouse administered with TH6 antibody, autoimmune gastritis was induced.

<Overall Review>

By administrating TH6 antibody, $T_{reg}$ cells could be depleted in vivo and develop autoimmune diseases. Since even Fab fragment of TH6 lack Fc portions, which bind to complements, etc., $T_{reg}$ cells were depleted the same as complete antibody; it is therefore clear that folate receptor 4 is necessary for $T_{reg}$ cells to survive, and there is a high possibility that TH6 antibody blocks the function of the folate receptor 4. In other words, $T_{reg}$ cells may be depleted by inhibiting the function of folate receptor 4.

Example 4

Effect of Anti-Folate Receptor 4 Antibody (TH6) for Treating tumor-1

<Experiment A>

Fibroblastoma Meth A cells (provided by Okayama University, $2\times10^5$) were subdermally administered to BALB/c mice, and 100 μg of monoclonal antibody (TH6 antibody) prepared in Reference Example 2 or rat IgG (product of Sigma Chemical Company) were intravenously administered to the mice on the same date of administration of the fibroblastoma Meth A cells. After administration, the longer and shorter axes of tumors were measured about every four days.

Figure 15:
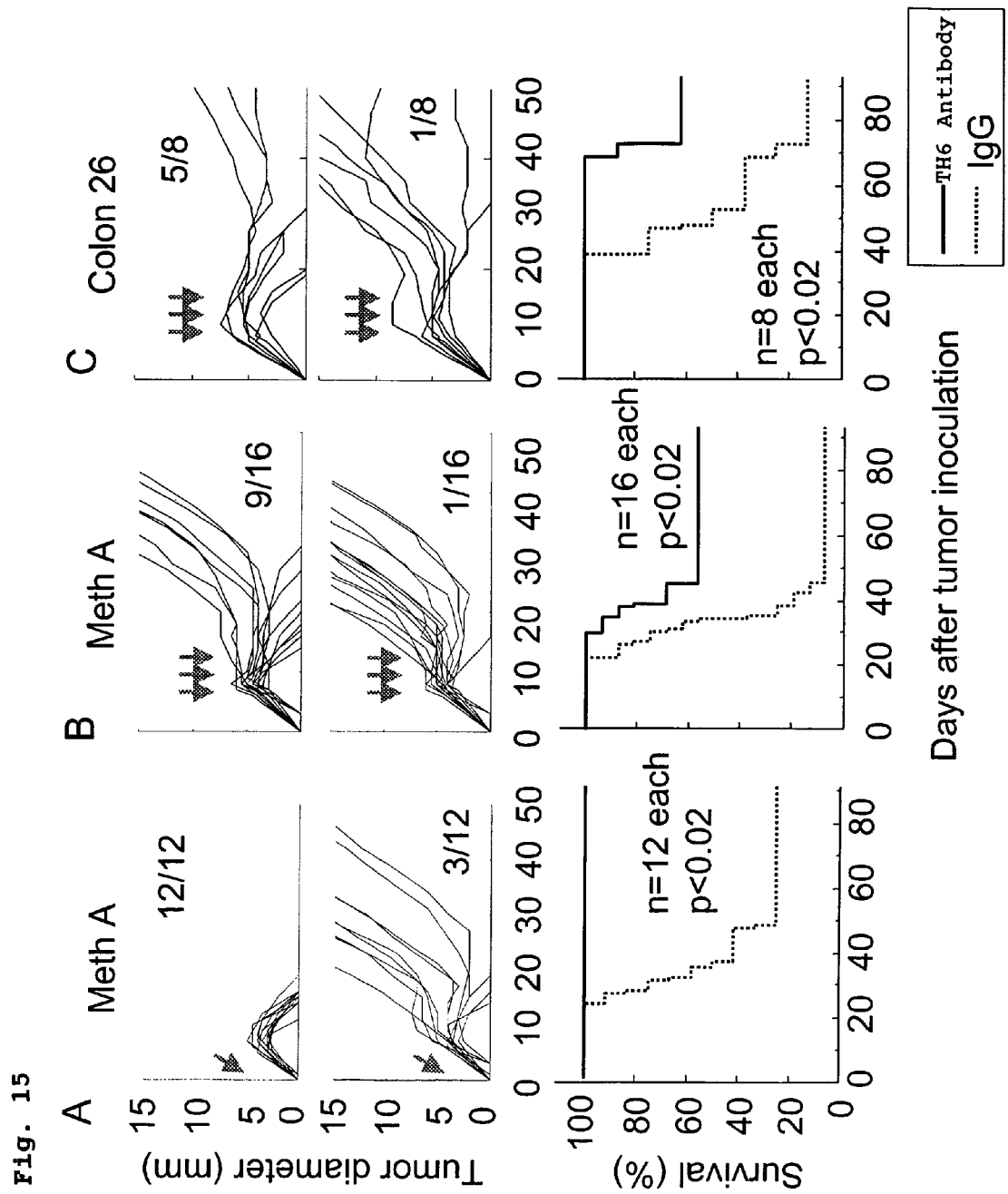
FIG. 15 shows the results of Example 4 in which the effect of anti-folate receptor 4 antibody (TH6) for treating tumors was measured.

FIG. 15 A shows the changes in average tumor axial lengths in the mice (top and middle charts), and survival rates after inoculation of tumor (bottom chart). Note that, in evaluating mouse survival, a mouse was considered to be dead if the average tumor axial length exceeded 15 mm. As is clear from FIG. 15A, in the IgG-administered group, the tumors did not persist in three mice out of 12; however, in the TH6 antibody-administered group, the tumors were rejected in all 12 mice.

<Experiment B>

Fibroblastoma Meth A cells (provided by Okayama University, $2\times10^5$) were subdermally administered to BALB/c mice on day zero, and 10 μg of monoclonal antibody (TH6 antibody) prepared in Reference Example 2 or rat IgG (product of Sigma Chemical Company) were administered three times, i.e., on days 8, 12, and 16, to those mice having a tumor at least 4 mm in axial length as of day 8.

FIG. 15B shows the changes in average tumor axial length in each mouse (top and middle charts), and the survival rate after inoculation of tumor (bottom chart). All 16 mice except one administered with IgG died because of the tumor; however, in 9 mice out of 16 administered with TH6 antibody, tumors were rejected. Based on the results, it was confirmed that administration of TH6 antibody is effective even for palpable Meth A tumors.

<Experiment C>

Colon-carcinoma cells Colon 26 ($2\times10^5$, provided by the Institute of Development, Aging and Cancer, Tohoku University) were subdermally administered to BALB/c mice on day zero of the experiment, and 10 μg of monoclonal antibody (TH6 antibody) prepared in Reference Example 2 or rat IgG (product of Sigma Chemical Company) were administered three times, i.e., on days 8, 12, and 16, to those mice having a tumor at least 3 mm of axial length as of day 8.

FIG. 15C shows changes in average tumor axial length (top and middle chart) in each mouse, and survival rate after inoculation of tumor (bottom chart). All eight IgG-administered mice except one died because of the tumor, but tumors were rejected in five out of eight TH6 antibody-administered mice.

<Overall Review>

It is known that a method for depleting $T_{reg}$ cells by administering anti-CD25 antibody is effective only if the administration of anti-CD25 antibody is conducted before tumor inoculation, and it is ineffective after tumor inoculation. It is assumed that this is because CD25 is highly expressed not only in $T_{reg}$ cells but also in activated T cells.

In contrast, by administering TH6 antibody, more than half of palpable tumors could be cured. It is assumed that this is because the effect of TH6 antibody could deplete just $T_{reg}$ cells without depleting activated T cells.

Example 5

Effect of Anti-Folate Receptor 4 Antibody (TH6) for Treating Tumor-2

<Experiment I>

After inoculating fibroblastoma Meth A cells ($2 \times 10^5$, provided by Okayama University) to the backs of BALB/c mice, 30 μg of anti-GITR antibody (DTA-1antibody; prepared by using mouse hybridoma DTA-1 cells; the mouse hybridoma DTA-1 cells are stored at the Institute for Frontier Medical Sciences, Kyoto University) were intravenously administered to the mice in order to increase immune response. Inguinal and under-foreleg lymph nodes and splenic cells were collected from the mice. The thus-collected cells were co-cultured with Meth A cells (the concentration of Meth A cells was $1/25^{th}$ to $1/5^{th}$ of lymphocytes) of which cell division was terminated by treating with mitomycin C, IL-2 was added in such a manner that the content of the IL-2 became 50 U/ml from the $6^{th}$ day of the culturing, and living cells were collected by the density centrifugation method using Lympholyte-M on the $9^{th}$ day of culturing. The thus-obtained cells (about $5 \times 10^7$ cells) were added to either 0.5 ml of culture medium containing TH6 antibody (1 μg/ml) prepared in Reference Example 2 or only 0.5 ml of culture medium, incubated on ice for 30 minutes, 5 ml of rabbit origin complement-containing liquid (product of Cedarlane, prepared by dissolving 1 vial of rabbit origin complement-containing liquid in 1 ml of sterile water, and diluting to $1/10$ using a RPMI solution containing 2% FCS) was added, and incubated at 37° C. for 30 minutes. Cells to which TH6 antibody was added before being treated with complement thereof was defined as cells treated with TH6 antibody and complement thereof (TH6$^{hi}$ depleted) and cells to which TH6 antibody was not added was defined as a whole. After washing, about $5 \times 10^5$ cells were reincubated using 50 μl of culture medium containing TH6 antibody (5 μg/ml), and FITC-labeled anti-rat antibody (product of Jackson ImmunoResarch) were added thereto in such a manner that the content of the FITC-labeled anti-rat antibody became 1 μg/ml, and reacted on ice for 30 minutes. After blocking with rat serum on ice for 20 minutes, PE-labeled anti-CD25 antibody (product of PharMingen Company), APC-labeled anti-CD4 antibody (product of PharMingen Company) or biotin-labeled anti-CD8 antibody (product of PharMingen Company) were added in such a manner that the content became 0.25 μg/ml, APC-labeled streptavidin was added in such a manner that the content thereof became 0.4 μg/ml and reacted on ice for 30 minutes, and FACS analysis was then conducted.

Figure 16:
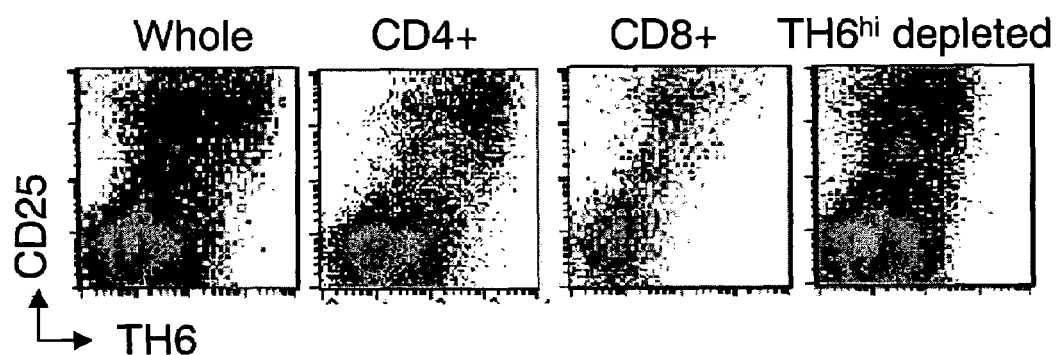
FIG. 16 shows the result of Experiment I in Example 5 in which various kinds of surface markers on cells that had been subjected to various cell treatments were measured.

FIG. 16 shows the results. In FIG. 16, the charts show, from the left, the analytical results for the cells without TH6 antibody treatment (whole), CD4$^+$ cells without TH6 antibody treatment, CD8$^+$ cells without TH6 antibody treatment, and cells treated with TH6 antibody and complement thereof (TH6$^{hi}$ depleted) after TH6 antibody treatment, respectively. In FIG. 16, the horizontal axes indicate PE fluorescence intensities (corresponding to expression of CD25), and the vertical axes indicate fluorescence intensities of FITC (corresponding to expression of folate receptor 4).

From these results, it was confirmed that, as the same as the cells stimulated with alloantigen, cells stimulated with tumor cells could be divided into three cell groups, i.e., having high expressions of both folate receptor 4 and CD25; moderate folate receptor 4 expression and moderate to high CD25 expression; and low expressions of both folate receptor 4 and CD25. The cells having high expressions of folate receptor 4 and CD25 existed in CD4$^+$ cells at high levels and was substantially not observed in CD8$^+$ cells. It was also confirmed that the cells having high expressions of folate receptor 4 and CD25 could be depleted by treating with TH6 antibody and complements thereof.

<Experiment II>

The cells cultured in Experiment I were divided into two groups, one without being treated with TH6 antibody (whole) and the other being treated with TH6 antibody and complements thereof (TH6$^{hi}$ depleted). Subsequently, $2 \times 10^6$ cells of each group were administered to different BALB/c nude mice, which had no T cells. After the administration (day zero), fibroblastoma Meth A cells ($2 \times 10^5$ cells, provided by Okayama University) were subdermally administered to the mice, and changes in diameter of the tumor were measured.

FIG. 17 shows the results, wherein changes in average tumor axial length of each mouse (left charts) and the survival rate after inoculation of tumor (right chart) are shown. Note that, in evaluating mouse survival, a mouse was considered to be dead when the average tumor axial length exceeded 15 mm or its body weight was significantly reduced, even if the mouse was actually not dead.

<Experiment III>

In the above-described Experiment II, either 90 days after tumor inoculation or at the time a mouse was considered to be dead, sera of the mice were collected and titers of anti-gastric parietal cell autoantibody of the sera collected from the mice were measured by the same method as in Example 3 of Experiment 3.

Figure 18:
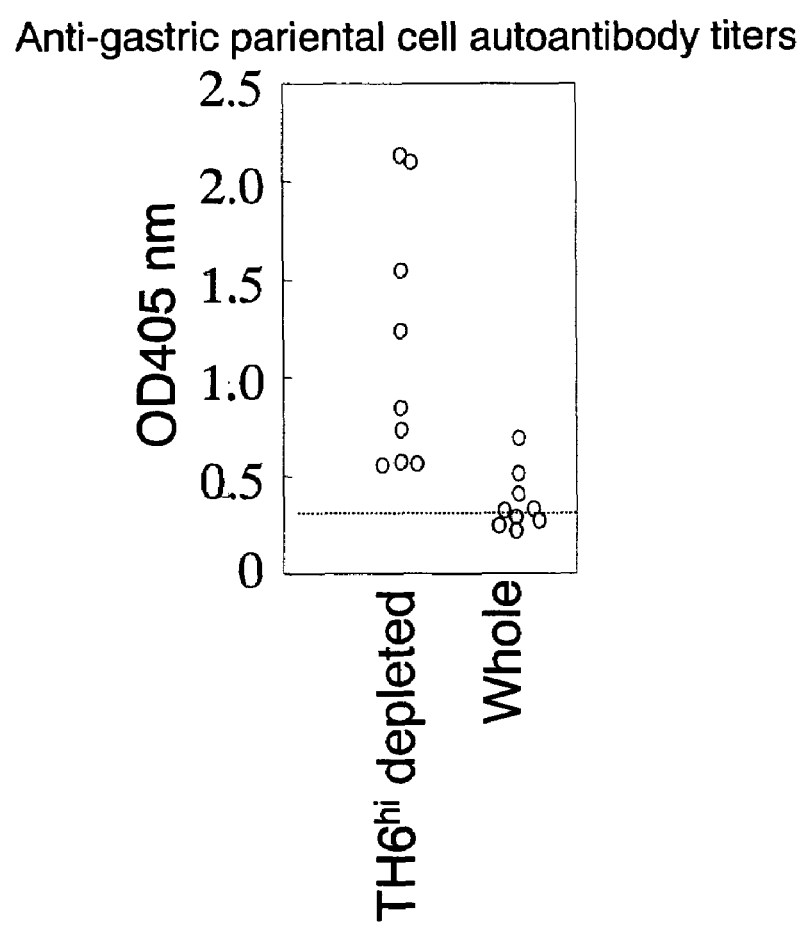
FIG. 18 shows the results of Experiment III of Example 5 in which anti-gastric parietal cell autoantibody titers in sera of BALB/c nude mice to which T cells without adding TH6 antibody (whole) or T cells that had been treated using TH6 antibody and complement thereof ($TH6^{hi}$ depleted) had been administered were measured.

FIG. 18 shows the results. The line in FIG. 18 indicates the mean OD405 nm value measured using sera collected from normal BALB/c mice. From these results, it became clear that mice administered the cells treated with TH6 antibody and complement (TH6$^{hi}$ depleted) had a higher antibody titer in the serum compared to the mice administered the cells that had not been treated with TH6 antibody (whole).

<Overall Review>

In mice administered with the cells from which cells with folate receptor 4 high expression were depleted (TH6$^{hi}$ depleted), proliferation of tumors was modest and the tumors were rejected in 5 mice out of 12. In contrast, when the entire cells after culturing (whole) was administered, proliferation reduction of tumors was observed in 2 or 3 out of 12 mice, but tumors grew as rapidly as in mice to which non-stimulated lymphocytes were administered in other mice, i.e., 9 or 10 out of the 12 mice. From these results, it is assumed that an intensive tumor immune response was induced by proliferating T cells having anti-tumor activity induced by stimulation in vitro, and depleting the $T_{reg}$ cells from the proliferated T cells while retaining activated T cells. In all mice administered with the cells from which cells having high folate receptor 4 expression had been removed (TH6$^{hi}$ depleted), anti-gastric parietal cell antibodies were observed, and the antibody titers thereof tended to be high. Therefore, it is assumed that in such mice, severe autoimmune diseases can be easily induced.

From the above-described results, it was confirmed that tumor immunity activity can be increased by inducing T cells which respond to a tumor in vitro, depleting the cells having high folate receptor 4 expressions from the T cells, and administering the thus obtained remaining cells in vivo.

Example 6

Assay of Human CD25$^+$CD4$^+$

Figure 19:
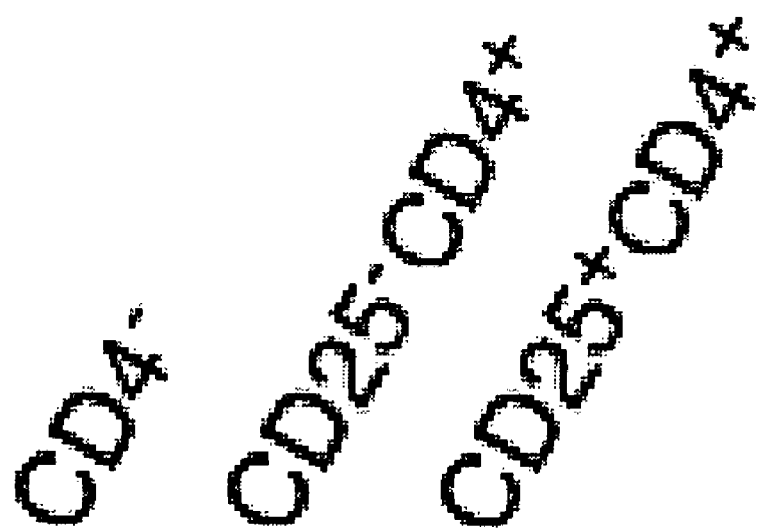
FIG. 19 shows the results of Example 6 in which expressions of folate receptor 4 and HPRT in human $CD4^-$ cells, $CD25^-CD4^+$ cells, and $CD25^+CD4^+$ cells were measured by PCR.

Peripheral blood mononuclear cells (PBMCs) were collected from a healthy donor and purified by gradient centrifugation using Ficoll-Paque™ plus (Amersham Biosciences). PBMCs were stained with magnetic beads conjugated anti-CD4 antibody (Miltenyi Biotec, human CD4 multisort kit) and CD4$^+$ cells were separated from CD4$^-$ cells with magnetic column. After dissociating the magnetic beads from the antibody, CD4$^+$ cells were stained with magnetic beads-conjugated anti-CD25 antibody. CD25$^+$CD4$^+$ cells were separated from CD25$^-$CD4$^+$ cells with magnetic column. RNAs were eluted from the sorted cells using an RNeasy mini kit (Qiagen). Reverse transcription of RNAs was performed with a SuperScript reverse transcriptase (Invitrogen). PCR for human folate receptor 4 fragment comprises a denaturation step at 94° C. for 2.5 minutes; followed by 5 cycles at 94° C. for 30 seconds, at 72° C. for 15 seconds; 5 cycles at 94° C. for 30 seconds, at 70° C. for 15 seconds, at 72° C. for 15 seconds; and 35 cycles at 94° C. for 30 seconds, at 68° C. for 15 seconds, at 72° C. for 15 seconds, using an advantage cDNA PCR kit (Clontech) with primers having the following sequences; ccccactctacaacttcagcctgtttcac and actcgctctccct-gcccactcgg. PCR for human HPRT fragment comprises a denaturation step at 94° C. for 2.5 minutes, followed by 30 cycles at 94° C. for 30 seconds, at 60° C. for 30 seconds, and at 72° C. for 45 seconds, with primers having the following sequences; tatggacaggactgaacgtcttgc and gacacaaacatgat-tcaaatccctga. DNA fragments with about 170 and 500 base pairs are shown for FLR4 and HPRT, respectively (see FIG. 19).

About human counterpart of the mouse FLR4, a gene sequence is predicted from a genomic sequence using a gene prediction method (Reference; O. Spiegelstein, J. D. Eudy, R. H. Funnell, Gene 258, 117-25 (Nov. 27, 2000)). This gene is also called as FRδ or "predicted gene: similar to folate receptor 3". We found that human CD25$^+$CD4$^+$ cells in peripheral blood express mRNAs for this predicted gene.

INDUSTRIAL APPLICABILITY

In the $T_{reg}$ cell detection and isolation methods of the present invention, by using the expressions of folate receptor 4 on the surface of cells as an indicator, $T_{reg}$ cells can be detected and isolated separately from activated T cells and/or naive T cells. Therefore, by applying the method of the present invention clinically, it becomes possible to selectively remove $T_{reg}$ cells from a patient, and selectively collect $T_{reg}$ cells and administer the collected $T_{reg}$ cells to a patient. Thus, the methods of the present invention are useful in immunosuppression after organ transplantation or cell therapy for treating malignant tumors.

The pharmaceutical composition for immunostimulation of the present invention can effectively exhibit the action of activated T cells by binding to $T_{reg}$ cells in vivo, and selectively reducing the number of $T_{reg}$ cells. The pharmaceutical composition of the present invention is particularly effective for treating malignant tumors, infectious diseases, etc., and is usable as an agent for treating these diseases.

The invention claimed is:

1. A method for treating a malignant tumor or infectious disease comprising:
    (a) collecting cells comprising T cells from a patient suffering from a malignant tumor or infectious disease;
    (b) inducing the T cells in the cells collected in (a) by subjecting the cells collected to an antigenic stimulus in vitro;
    (c) depleting from the resulting cells of (b), cells having the highest folate receptor 4 expression, so as to obtain cells comprising T cells from which regulatory T cells have been removed; and
    (d) administering the resulting depleted cells obtained in (c) to the patient.

2. The method of claim 1, wherein step (c) is carried out by the method comprising:
    (i) measuring expression of folate receptor 4 on the surface of the T cells;
    (ii) detecting regulatory T cells using the expression as an indicator; and
    (iii) depleting regulatory T cells having the highest folate receptor 4 expression.

3. The method of claim 1, wherein the folate receptor 4 expression is measured using an anti-folate receptor 4 antibody or a folate receptor 4-binding fragment.

* * * * *